(12) United States Patent
Ortyn et al.

(10) Patent No.: US 8,009,189 B2
(45) Date of Patent: *Aug. 30, 2011

(54) EXTENDED DEPTH OF FIELD IMAGING FOR HIGH SPEED OBJECT ANALYSIS

(75) Inventors: William Ortyn, Bainbridge Island, WA (US); David Basiji, Seattle, WA (US); Keith Frost, Seattle, WA (US); Luchuan Liang, Woodinville, WA (US); Richard Bauer, Kirkland, WA (US); Brian Hall, Seattle, WA (US); David Perry, Woodinville, WA (US)

(73) Assignee: Amnis Corporation, Seattle, WA (US)

( * ) Notice: Subject to any disclaimer, the term of this patent is extended or adjusted under 35 U.S.C. 154(b) by 735 days.
This patent is subject to a terminal disclaimer.

(21) Appl. No.: 12/132,394

(22) Filed: Jun. 3, 2008

(65) Prior Publication Data
US 2008/0234984 A1  Sep. 25, 2008

Related U.S. Application Data

(63) Continuation of application No. 11/609,269, filed on Dec. 11, 2006, application No. 12/132,394, which is a continuation of application No. 11/123,610, filed on May 4, 2005, now Pat. No. 7,450,229, and a continuation-in-part of application No. 10/628,662, filed on Jul. 28, 2003, now Pat. No. 6,975,400, which is a continuation-in-part of application No. 09/976,257, filed on Oct. 12, 2001, now Pat. No. 6,608,682, which is a continuation-in-part of application No. 09/820,434, filed on Mar. 29, 2001, now Pat. No. 6,473,176, said application No. 09/820,434 is a continuation-in-part of application No. 09/538,604, filed on Mar. 29, 2000, now Pat. No. 6,211,955, which is a continuation-in-part of application No. 09/490,478, filed on Jan. 24, 2000, now Pat. No. 6,249,341, said application No. 09/976,257 , said application No. 11/123,610.

(60) Provisional application No. 60/748,888, filed on Dec. 9, 2005, provisional application No. 60/567,911, filed on May 4, 2004, provisional application No. 60/240,125, filed on Oct. 12, 2000, provisional application No. 60/117,203, filed on Jan. 25, 1999.

(51) Int. Cl.
*G01J 3/28* (2006.01)
*G01J 3/51* (2006.01)

(52) U.S. Cl. ............ 348/80; 356/326; 356/73; 356/419; 382/133

(58) Field of Classification Search .................. 348/80, 348/79; 356/326, 73, 419; 382/133
See application file for complete search history.

(56) References Cited

U.S. PATENT DOCUMENTS
3,497,690 A    2/1970    Bahr et al. ............... 250/461.2
(Continued)

FOREIGN PATENT DOCUMENTS
EP    0 154 404    9/1985
(Continued)

OTHER PUBLICATIONS

Amann et al., "Fluorescent-Oligonucleotide Probing of Whole Cells for Determinative, Phylogenetic, and Environmental Studies in Microbiology," *Journal of Bacteriology* vol. 172, No. 2: 762-770, Feb. 1990.
(Continued)

*Primary Examiner* — Haresh N Patel
(74) *Attorney, Agent, or Firm* — Ronald M. Anderson

(57) ABSTRACT

A high speed, high-resolution flow imaging system is modified to achieve extended depth of field imaging. An optical distortion element is introduced into the flow imaging system. Light from an object, such as a cell, is distorted by the distortion element, such that a point spread function (PSF) of the imaging system is invariant across an extended depth of field. The distorted light is spectrally dispersed, and the dispersed light is used to simultaneously generate a plurality of images. The images are detected, and image processing is used to enhance the detected images by compensating for the distortion, to achieve extended depth of field images of the object. The post image processing preferably involves de-convolution, and requires knowledge of the PSF of the imaging system, as modified by the optical distortion element.

35 Claims, 15 Drawing Sheets

U.S. PATENT DOCUMENTS

| | | | |
|---|---|---|---|
| 3,555,280 A | 1/1971 | Richards, Jr. | 250/201 |
| 3,586,760 A | 6/1971 | Dillenburger | 348/339 |
| 3,922,069 A | 11/1975 | Kishikawa et al. | 359/633 |
| 4,313,734 A | 2/1982 | Leuvering | 23/230 |
| 4,414,575 A | 11/1983 | Yamamoto et al. | 348/350 |
| 4,635,293 A | 1/1987 | Watanabe | 382/130 |
| 4,662,742 A | 5/1987 | Chupp | 356/39 |
| 4,677,680 A | 6/1987 | Harima et al. | 382/112 |
| 4,703,017 A | 10/1987 | Campbell et al. | 436/501 |
| 4,737,932 A | 4/1988 | Baba | 364/900 |
| 4,770,992 A | 9/1988 | Van den Engh et al. | 435/6 |
| 4,777,525 A | 10/1988 | Preston, Jr. | 348/111 |
| 4,786,165 A | 11/1988 | Yamamoto et al. | 356/23 |
| 4,845,197 A | 7/1989 | Petersen et al. | 530/387 |
| 4,857,453 A | 8/1989 | Ullman et al. | 435/7 |
| 5,096,807 A | 3/1992 | Leaback | 435/6 |
| 5,107,522 A | 4/1992 | Kitayama et al. | 375/97 |
| 5,122,453 A | 6/1992 | Martin et al. | 435/7.24 |
| 5,141,609 A | 8/1992 | Sweedler et al. | 204/452 |
| 5,153,916 A | 10/1992 | Inagaki et al. | 382/151 |
| 5,159,397 A | 10/1992 | Kosaka et al. | 356/73 |
| 5,159,398 A | 10/1992 | Maekawa et al. | 356/73 |
| 5,159,642 A | 10/1992 | Kosaka | 382/134 |
| 5,247,339 A | 9/1993 | Ogino | 356/73 |
| 5,247,340 A | 9/1993 | Ogino | 356/73 |
| 5,257,182 A | 10/1993 | Luck et al. | 364/413.1 |
| 5,272,354 A | 12/1993 | Kosaka | 250/574 |
| 5,351,311 A | 9/1994 | Rogers et al. | 382/156 |
| 5,372,936 A | 12/1994 | Fraatz et al. | 435/34 |
| 5,422,712 A | 6/1995 | Ogino | 356/73 |
| 5,436,144 A | 7/1995 | Stewart et al. | 435/91.2 |
| 5,444,527 A | 8/1995 | Kosaka | 356/73 |
| 5,459,240 A | 10/1995 | Foxwell et al. | 530/328 |
| 5,471,294 A | 11/1995 | Ogino | 356/73 |
| 5,547,849 A | 8/1996 | Baer et al. | 435/7.24 |
| 5,548,349 A | 8/1996 | Mizuguchi et al. | 348/766 |
| 5,548,395 A | 8/1996 | Kosaka | 356/73 |
| 5,568,315 A | 10/1996 | Shuman | 359/487 |
| 5,596,401 A | 1/1997 | Kusuzawa | 356/23 |
| 5,621,460 A | 4/1997 | Hatlestad et al. | 348/265 |
| 5,625,048 A | 4/1997 | Tsien et al. | 536/23.4 |
| 5,633,503 A | 5/1997 | Kosaka | 250/458.1 |
| 5,644,388 A | 7/1997 | Maekawa et al. | 356/73 |
| 5,674,743 A | 10/1997 | Ulmer | 435/287.2 |
| 5,686,960 A | 11/1997 | Sussman et al. | 348/335 |
| 5,695,934 A | 12/1997 | Brenner | 435/6 |
| 5,733,721 A | 3/1998 | Hemstreet, III et al. | 435/6 |
| 5,754,291 A | 5/1998 | Kain | 356/338 |
| 5,760,899 A | 6/1998 | Eismann | 356/326 |
| 5,764,792 A | 6/1998 | Kennealy | 382/133 |
| 5,784,162 A | 7/1998 | Cabib et al. | 356/456 |
| RE35,868 E | 8/1998 | Kosaka | 250/574 |
| 5,828,776 A | 10/1998 | Lee et al. | 382/133 |
| 5,831,723 A | 11/1998 | Kubota et al. | 356/73 |
| 5,844,670 A | 12/1998 | Morita et al. | 356/124 |
| 5,848,123 A | 12/1998 | Strommer | 378/98.8 |
| 5,855,753 A | 1/1999 | Trau et al. | 204/484 |
| 5,900,942 A | 5/1999 | Spiering | 356/400 |
| 5,926,283 A | 7/1999 | Hopkins | 356/419 |
| 5,929,986 A | 7/1999 | Slater et al. | 356/326 |
| 5,959,953 A | 9/1999 | Alon | 369/44.41 |
| 5,985,549 A | 11/1999 | Singer et al. | 435/6 |
| 5,986,061 A | 11/1999 | Pestka | 530/352 |
| 6,007,994 A | 12/1999 | Ward et al. | 435/6 |
| 6,007,996 A | 12/1999 | McNamara et al. | 435/6 |
| 6,014,468 A | 1/2000 | McCarthy et al. | 382/254 |
| 6,066,459 A | 5/2000 | Garini et al. | 435/6 |
| 6,108,082 A | 8/2000 | Pettipiece et al. | 356/302 |
| 6,115,119 A | 9/2000 | Sieracki et al. | 356/337 |
| 6,116,739 A | 9/2000 | Ishihara et al. | 353/31 |
| 6,156,465 A | 12/2000 | Cao et al. | 430/30 |
| 6,159,686 A | 12/2000 | Kardos et al. | 435/6 |
| 6,210,973 B1 | 4/2001 | Pettit | 436/172 |
| 6,211,955 B1 | 4/2001 | Basiji et al. | 356/326 |
| 6,229,913 B1 | 5/2001 | Nayar et al. | 382/154 |
| 6,249,314 B1 | 6/2001 | Yamamoto et al. | 348/242 |
| 6,249,341 B1 | 6/2001 | Basiji et al. | 356/73 |
| 6,256,096 B1 | 7/2001 | Johnson | 356/335 |
| 6,259,807 B1 | 7/2001 | Ravkin | 381/133 |
| 6,330,081 B1 | 12/2001 | Scholten | 358/463 |
| 6,330,361 B1 | 12/2001 | Mitchell et al. | 382/211 |
| 6,381,363 B1 | 4/2002 | Murching et al. | 382/164 |
| 6,473,176 B2 | 10/2002 | Basiji et al. | 356/326 |
| 6,507,391 B2 | 1/2003 | Basiji et al. | 356/28 |
| 6,510,319 B2 | 1/2003 | Baum et al. | 455/442 |
| 6,519,355 B2 | 2/2003 | Nelson | 382/133 |
| 6,522,781 B1 | 2/2003 | Norikane et al. | 382/203 |
| 6,532,061 B2 | 3/2003 | Ortyn et al. | 356/28 |
| 6,548,259 B2 | 4/2003 | Ward et al. | 435/6 |
| 6,549,664 B1 | 4/2003 | Daiber et al. | 382/232 |
| 6,563,583 B2 | 5/2003 | Ortyn et al. | 356/400 |
| 6,580,504 B1 | 6/2003 | Basiji et al. | 356/338 |
| 6,583,865 B2 | 6/2003 | Basiji et al. | 356/73 |
| 6,608,680 B2 | 8/2003 | Basiji et al. | 356/338 |
| 6,608,682 B2 | 8/2003 | Ortyn et al. | 356/419 |
| 6,618,140 B2 | 9/2003 | Frost et al. | 356/317 |
| 6,620,591 B1 | 9/2003 | Dunlay et al. | 435/7.2 |
| 6,658,143 B2 | 12/2003 | Hansen et al. | 382/133 |
| 6,671,044 B2 | 12/2003 | Ortyn et al. | 356/326 |
| 6,671,624 B1 | 12/2003 | Dunlay et al. | 702/19 |
| 6,707,551 B2 | 3/2004 | Ortyn et al. | 356/338 |
| 6,716,588 B2 | 4/2004 | Sammak et al. | 435/7.23 |
| 6,727,066 B2 | 4/2004 | Kaser | 435/6 |
| 6,763,149 B2 | 7/2004 | Riley et al. | 382/294 |
| 6,778,263 B2 | 8/2004 | Ortyn et al. | 356/28 |
| 6,875,973 B2 | 4/2005 | Ortyn et al. | 250/201.3 |
| 6,906,792 B2 | 6/2005 | Ortyn et al. | 356/28.5 |
| 6,927,922 B2 | 8/2005 | George et al. | 359/708 |
| 6,934,408 B2 | 8/2005 | Frost et al. | 382/129 |
| 6,947,128 B2 | 9/2005 | Basiji et al. | 356/73 |
| 6,947,136 B2 | 9/2005 | Ortyn et al. | 356/338 |
| 6,975,400 B2 | 12/2005 | Ortyn et al. | 356/419 |
| 7,006,710 B2 | 2/2006 | Riley et al. | 382/294 |
| 7,033,819 B2 | 4/2006 | Kim et al. | 435/29 |
| 7,042,639 B1 | 5/2006 | McDowell | 359/398 |
| 7,050,620 B2 | 5/2006 | Heckman | 382/133 |
| 7,057,732 B2 | 6/2006 | Jorgenson et al. | 356/445 |
| 7,079,708 B2 | 7/2006 | Riley et al. | 382/294 |
| 7,087,877 B2 | 8/2006 | Ortyn et al. | 250/201.2 |
| 7,139,415 B2 | 11/2006 | Finkbeiner | 382/128 |
| 7,190,832 B2 | 3/2007 | Frost et al. | 382/173 |
| 7,221,457 B2 | 5/2007 | Jorgenson et al. | 356/445 |
| 7,289,205 B2 | 10/2007 | Yaroslavsky et al. | 356/417 |
| 7,315,357 B2 | 1/2008 | Ortyn et al. | 356/73 |
| 7,450,229 B2 * | 11/2008 | Ortyn et al. | 356/326 |
| 7,567,695 B2 | 7/2009 | Frost et al. | 382/129 |
| 2001/0006416 A1 | 7/2001 | Johnson | 356/73 |
| 2001/0012620 A1 | 8/2001 | Rich | 435/7.1 |
| 2002/0126275 A1 | 9/2002 | Johnson | 356/317 |
| 2002/0146734 A1 | 10/2002 | Ortyn et al. | 435/6 |
| 2002/0196980 A1 | 12/2002 | Dowski, Jr. | 382/232 |
| 2003/0048931 A1 | 3/2003 | Johnson et al. | 382/128 |
| 2003/0049701 A1 | 3/2003 | Muraca | 435/7.23 |
| 2003/0059093 A1 | 3/2003 | Rosania et al. | 382/128 |
| 2003/0104439 A1 | 6/2003 | Finch | 435/6 |
| 2004/0093166 A1 | 5/2004 | Kil | 702/19 |
| 2004/0111220 A1 | 6/2004 | Ochs et al. | 702/19 |
| 2004/0228005 A1 | 11/2004 | Dowski, Jr. | 359/671 |
| 2004/0241759 A1 | 12/2004 | Tozer et al. | 435/7.2 |
| 2005/0014129 A1 | 1/2005 | Cliffel et al. | 435/4 |
| 2006/0246481 A1 | 11/2006 | Finch et al. | 435/6 |
| 2006/0257884 A1 | 11/2006 | Brawley et al. | 435/6 |
| 2007/0054350 A1 | 3/2007 | Walker, Jr. | 435/34 |
| 2008/0240539 A1 | 10/2008 | George et al. | 382/133 |
| 2009/0202130 A1 | 8/2009 | George et al. | 382/133 |

FOREIGN PATENT DOCUMENTS

| | | |
|---|---|---|
| EP | 0 280 559 | 8/1988 |
| EP | 0 281 327 | 6/1993 |
| EP | 0 372 707 | 3/1996 |
| EP | 0 950 890 | 10/1999 |
| EP | 1 316 793 | 6/2003 |
| WO | WO 88/08534 | 11/1988 |
| WO | WO 90/10715 | 9/1990 |
| WO | WO 95/20148 | 7/1995 |
| WO | WO 97/26333 | 7/1997 |
| WO | WO 98/53093 | 11/1998 |

| | | |
|---|---|---|
| WO | WO 98/53300 | 11/1998 |
| WO | WO 99/24458 | 5/1999 |
| WO | WO 99/64592 | 12/1999 |
| WO | WO 00/06989 | 2/2000 |
| WO | WO 00/14545 | 3/2000 |
| WO | WO 00/42412 | 7/2000 |
| WO | WO 01/11341 | 2/2001 |
| WO | WO 01/46675 | 6/2001 |
| WO | WO 02/17622 | 2/2002 |
| WO | WO 02/18537 | 3/2002 |
| WO | WO 02/35474 | 5/2002 |
| WO | WO 02/073200 | 9/2002 |
| WO | WO 02/079391 | 10/2002 |

OTHER PUBLICATIONS

Arkesteijn et al., "Chromosome Specific DNA Hybridization in Suspension for Flow Cytometric Detection of Chimerism in Bone Marrow Transplantation and Leukemia," *Cytometry* 19: 353-360, Apr. 1995.

Bains et al., "Flow Cytometric Quantitation of Sequence-Specific mRNA in Hemopoietic Cell Suspension by Primer-Induced in Situ (PRINS) Fluorescent Nucleotide Labeling," *Experimental Cell Research* 208: 321-326, Sep. 1993.

Callet-Bauchu et al., "Distribution of the cytogenetic abnormality +i(3)(q10) in persistent polyclonal B-cell lymphocytosis: a FICTION study in three cases," *British Journal of Haematology* 99: 531-536, Dec. 1997.

Ding et al., "Characterization and Quantitation of NF-κB Nuclear Translocation Induced by Interleukin-1 and Tumor Necrosis Factor-α," *The Journal of Biological Chemistry* vol. 273, No. 44: 28897-28905, Oct. 30, 1998.

Dragowska et al., "Measurement of DNA repeat sequence by flow cytometry," *Cytometry* Supplement 7: 51, Oct. 1994.

Fernandez-Lago et al., "Fluorescent Whole-Cell Hybridization with 16S rRNA-Targeted Oligonucleotide Probes To Identify *Brucella* spp. By Flow Cytometry," *Journal of Clinical Microbiology* vol. 38, No. 7: 2768-2771, Jul. 2000.

Gordy et al., "Visualization of Antigen Presentation by Actin-Mediated Targeting of Glycolipid-Enriched Membrane Domains to the Immune Synapse of B cell APCs." *Journal of Immunology* vol. 172, No. 4: 2030-2038, Feb. 15, 2004.

Hultdin et al., "Telomere analysis by fluorescence in situ hybridization and flow cytometry," *Nucleic Acids Research* vol. 26, No. 16: 3651-3656, Aug. 15, 1998.

Lauzon et al., "Flow Cytometric Measurement of Telomere Length," *Cytometry* 42: 159-164, Jun. 2000.

Levron et al., "Sperm chromosome abnormalities in men with severe male factor infertility who are undergoing in vitro fertilization with intracytoplasmic sperm injection," *Fertility and Sterility* vol. 76, No. 3: 479-484, Sep. 2001.

Majno et al., "Apoptosis, Oncosis, and Necrosis *An Overview of Cell Death*," *American Journal of Pathology* vol. 146, No. 1: 3-15, Jan. 1, 1995.

Patterson et al., "Detection of HIV-1 DNA and Messenger RNA in Individual Cells by PCR-Driven in Situ Hybridization and Flow Cytometry," *Science* 260: 976-979, May 14, 1993.

Ried et al., "Simultaneous visualization of seven different DNA probes by in situ hybridization using combinatorial fluorescence and digital imaging microscopy," *Proceedings of the National Academy of Sciences: Genetics* 89: 1388-1392, Feb. 1992.

Robbins et al., "Aneuploidy in sperm of Hodgkin's disease patients receiving NOVP chemotherapy," *The American Journal of Human Genetics* vol. 55, No. 3—Supplement: A68 (371), Sep. 1994.

Rufer et al., "Telomere length dynamics in human lymphocyte subpopulations measured by flow cytometry," *Nature Biotechnology* 16: 743-747, Aug. 1998.

Wyrobek et al., "Smokers produce more aneuploid sperm than non-smokers," *The American Society of Human Genetics*, 45th Annual Meeting, A131: 737, Oct. 24-28, 1995.

Wyrobek et al., "Fluorescence in Situ Hybridization to Y Chromosomes in Decondensed Human Sperm Nuclei," *Molecular Reproduction and Development* 27: 200-208, 1990.

Biggs, David S.C., and Mark Andrews. "Acceleration of iterative image restoration algorithms" *Applied Optics* vol. 36, No. 8. Mar. 10, 1997.

Ong, Sim Heng. 1985. Development of a System for Imaging and Classifying Biological Cells in a Flow Cytometer. Doctor of Philosophy Thesis. University of Sydney, School of Electrical Engineering. (August).

Ong, S.H. et al. 1987. "Development of an Image Flow Cytometer." *Analytical and Quantitative Cytology and Histology*. XIVth International Conference on Medical and Biological Engineering and the VIIth International Conference on Medical Physics, Finland. (August): 375-382.

Tucker, Sara C., W. Thomas Cathey and Edward R. Dowski, Jr. "Extended depth of field and aberration control for inexpensive digital microscope systems" *Optics Express* vol. 4, No. 11. May 24, 1999. pp. 467-474.

Oberholzer et al., "Methods in quantitative image analysis." *Histochem Cell Biol*, vol. 105: 333-355, 1996.

Ferraro et al., "Extended focused image in microscopy by digital holography." *Optics Express*, vol. 13, No. 18: 6738-6749, 2005.

\* cited by examiner

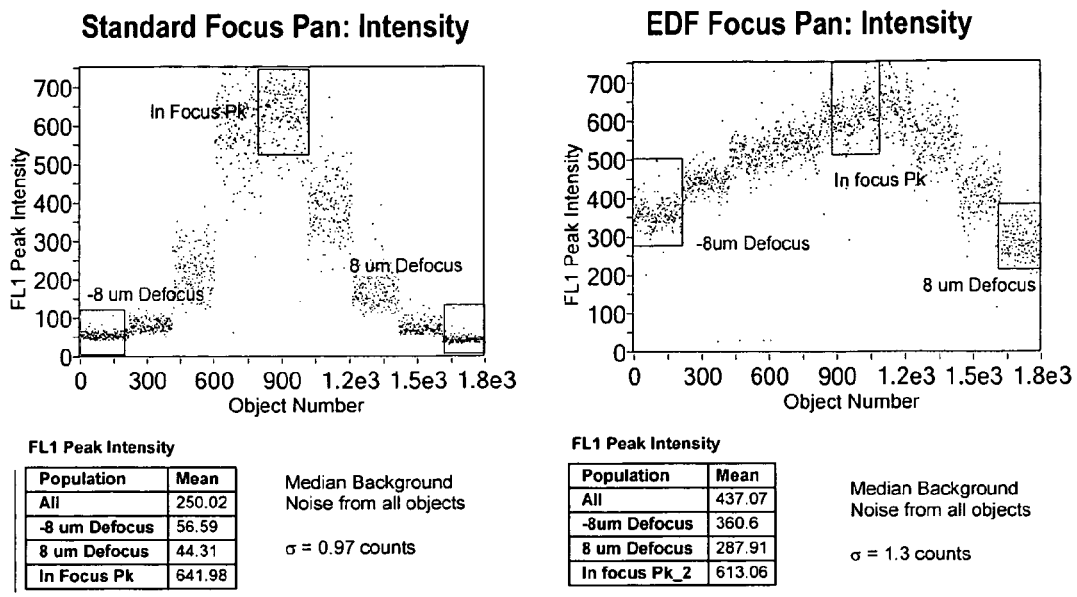
FIG. 15A – PRIOR ART   FIG. 16A
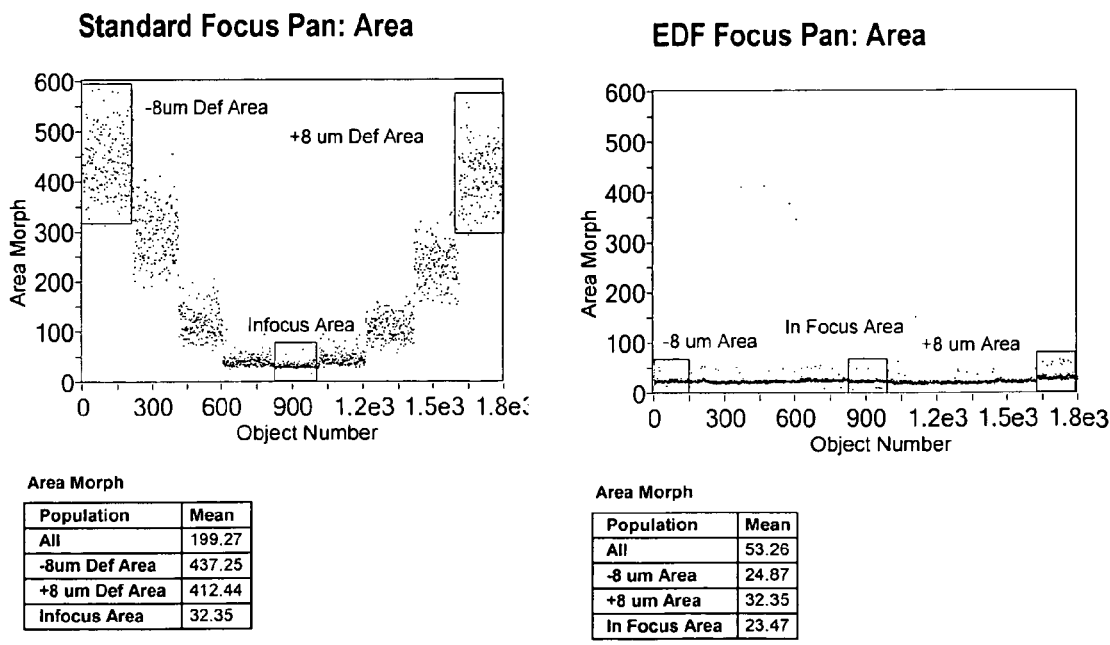
FIG. 15B – PRIOR ART   FIG. 16B

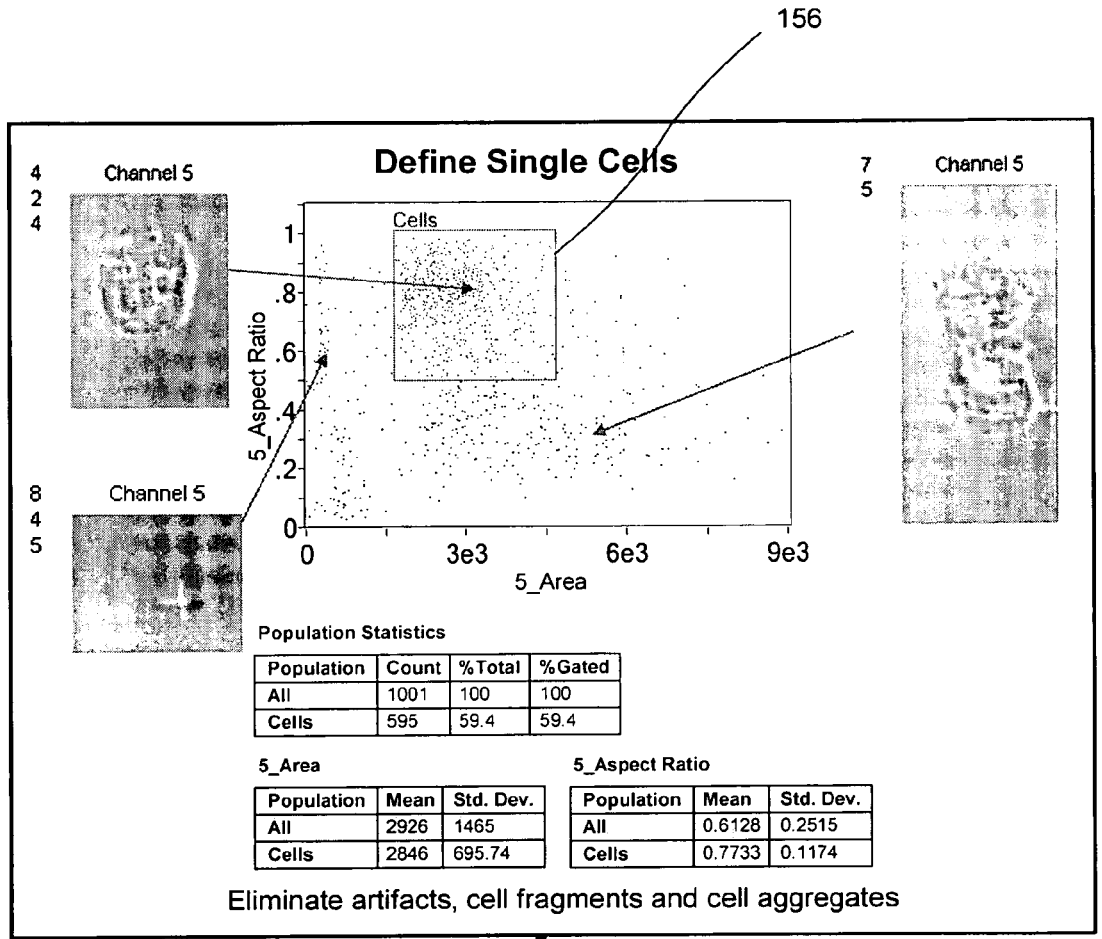
FIG. 18
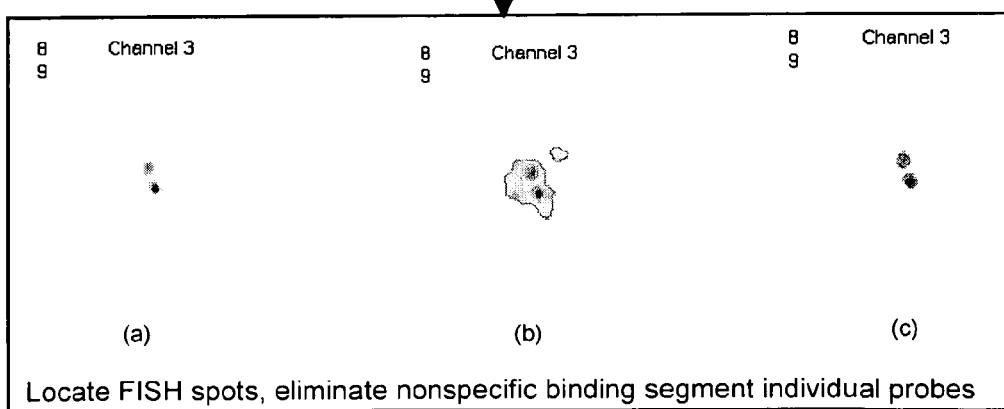
FIG. 19A    FIG. 19B    FIG. 19C

Standard Mono Refined

EDF Mono Refined

Standard Mono False Positive

EDF Mono False Positive

Standard Disomy Refined

EDF Disomy Refined

Standard Disomy False Positive

EDF Disomy False Positive

EXTENDED DEPTH OF FIELD IMAGING FOR HIGH SPEED OBJECT ANALYSIS

RELATED APPLICATIONS

This application is a continuation of a U.S. patent application Ser. No. 11/609,269, now copending, filed on Dec. 11, 2006, the benefit of the filing date of which is hereby claimed under 35 U.S.C. §120, which itself is based on a prior provisional application, Ser. No. 60/748,888, filed on Dec. 9, 2005, the benefit of the filing date of which is hereby claimed under 35 U.S.C. §119(e).

In addition, this application is also a continuation application based on a U.S. prior copending conventional application Ser. No. 11/123,610, filed on May 4, 2005, which itself is based on a prior provisional application Ser. No. 60/567,911, filed on May 4, 2004, which issued as U.S. Pat. No. 7,450,229 on Nov. 11, 2008, and which is also a continuation-in-part of prior patent application Ser. No. 10/628,662, filed on Jul. 28, 2003, which issued as U.S. Pat. No. 6,975,400 on Dec. 13, 2005, which itself is a continuation-in-part application of prior patent application Ser. No. 09/976,257, filed on Oct. 12, 2001, which issued as U.S. Pat. No. 6,608,682 on Aug. 19, 2003, which itself is a continuation-in-part application of prior patent application Ser. No. 09/820,434, filed on Mar. 29, 2001, which issued as U.S. Pat. No. 6,473,176 on Oct. 29, 2002, which itself is a continuation-in-part application of prior patent application Ser. No. 09/538,604, filed on Mar. 29, 2000, which issued as U.S. Pat. No. 6,211,955 on Apr. 3, 2001, which itself is a continuation-in-part application of prior application patent application Ser. No. 09/490,478, filed on Jan. 24, 2000, which issued as U.S. Pat. No. 6,249,341 on Jun. 19, 2001, which itself is based on prior provisional patent application Ser. No. 60/117,203, filed on Jan. 25, 1999, the benefit of the filing dates of which is hereby claimed under 35 U.S.C. §120 and 35 U.S.C. §119(e).

Patent application Ser. No. 09/976,257, noted above, filed on Oct. 12, 2001, which issued as U.S. Pat. No. 6,608,682 on Aug. 19, 2003, is also based on prior provisional application Ser. No. 60/240,125, filed on Oct. 12, 2000, the benefit of the filing date of which is hereby claimed under 35 U.S.C. §119(e).

GOVERNMENT RIGHTS

This invention was funded at least in part with grants (No. 9 R44 CA01798-02 and 1 R43 GM58956-01) from the National Institutes of Health (NIH) and a contract (NNA05CR09C) from the National Aeronautics and Space Administration (NASA), and the U.S. government may have certain rights in this invention.

BACKGROUND

Conventional imaging systems are challenged to provide adequate low-light, high-resolution imaging. Objective components used in high-resolution imaging systems need to have very high numeric aperture (NA) values. Unfortunately, a high NA value of the objective component results in a very small depth of field in which to view target objects. A small depth of field raises significant challenges in achieving and maintaining focus of target objects to be viewed during low-light, high-resolution imaging. If focus of a target object is not achieved and maintained, the resultant defocused image of the target object at a detector is spread over an unacceptably large area of the detector, with a loss in spatial resolution and a decrease in the signal-to-noise ratio associated with the image of the target object.

Confocal microscopy provides the ability to image cross sections of a cell ("optical sectioning") for the purpose of generating a three-dimensional map of cellular structures, or to synthesize a single two-dimensional image in which all cellular structures are in focus. These capabilities are desirable for a wide range of cell analysis applications, including co-localization studies, quantifying the translocation of molecules between cellular compartments, and the enumeration of fluorescence in situ hybridization probes randomly located in a nucleus. Although confocal microscopy provides a highly detailed view of the cell, the repeated scanning required significantly reduces image acquisition rates, and can in some cases, induce photo-bleaching of fluorescent probes.

Currently confocal microscopy is limited by the length of time required to capture imagery, the types of signals that can be collected simultaneously, and the limitation that the cells be immobilized on a solid support. The relatively slow speed of confocal microscopy can be a limiting factor for many applications. Commonly-studied cellular phenomena, including signaling, internalization of surface-bound factors, chromosomal defects, and various morphological transformations, can be subject to high cell-to-cell variation, occur over a wide and continuous range of values, or occur at low frequencies within a heterogeneous mixture of cells. Therefore, the study of such phenomena can require the observation and analysis of thousands of cells, and the application of statistical analysis in order to reach robust and repeatable scientific conclusions. In such cases, it is often impractical to employ confocal microscopy, due to the low throughput of the technique, despite the wealth of information it can provide for each cell.

In the alternative, conventional fluorescence imaging is generally much faster than confocal image stacking and can provide good spatial resolution and fluorescence sensitivity, when employing high NA objectives. However, conventional fluorescence microscopy is subject to a tradeoff between NA and depth of field. As the NA is increased to improve light collection and increase spatial resolution, the depth of field is reduced by the square of the NA change. Therefore, images of weakly fluorescent signals and cellular structures located outside the ideal plane of focus can be compromised. This effect is most readily observed in experiments employing Fluorescence In Situ Hybridization (FISH) probes that are typically under one micron in size and are comprised of a limited number of fluorescent molecules, which can be distributed throughout the nucleus or cytoplasm of a cell. A slight defocus may preclude the detection of dim probes, or cause multiple probes located in close proximity to blur into each other. Larger amounts of defocus can cause substantial blur, rendering a FISH spot unrecognizable in an image. These tradeoffs for increased speed over the highly focused imagery produced by confocal image stacking are generally not acceptable, given that conventional microscopy, even in automated form, is still slow compared to flow cytometry. As a result, many studies of cellular phenomena employ both flow cytometry (for the high throughput study of large cell populations) and confocal microscopy (for the detailed imaging of selected individual cells).

The ImageStream™ flow imaging system was developed in part to address the gap between the slow, but detailed information obtained by confocal microscopy and the fast, but limited cellular information gleaned by flow cytometry. The ImageStream™ system collects six simultaneous multimode images (brightfield, darkfield, and up to four different fluorescence colors) from cells in flow. High fluorescence sensitivity and resolution are achieved by using 0.75 NA optics and a 0.5 micron pixel size.

Several attempts have been made to extend the depth of field of such a flow imaging system. For example, U.S. Pat. No. 6,583,865 (the disclosure and drawings of which are hereby specifically incorporated herein by reference) describes the use of a flow imaging system having a tilted detector (or a sample flow path that is tilted relative to the detector) that effectively increases the depth of field for a more accurate enumeration of structures and probes within a cell. The technique can be used in connection with a pulsed light source to produce multiple images of a moving object at different focal planes, or it can employ a continuous light source to produce a single composite image incorporating information from the object at multiple focal planes. The pulsed light source variant is limited in fluorescence sensitivity because each image has a relatively short signal integration time. The continuous light source variant is limited in image quality because the composite image contains both in-focus and out-of-focus information at every location in the cell. Hence, there is a need for a high speed imaging system having an extended depth of field as well as both high fluorescence sensitivity and excellent image quality.

U.S. Pat. No. 7,009,651 (the disclosure and drawings of which are hereby also specifically incorporated herein by reference) describes a flow imaging system in which light from an object is split into a plurality of optical paths, and one or more of the optical paths are defocused relative to the default focal plane of the system, to similarly increase the depth of field. U.S. Pat. No. 6,211,955 (the disclosure and drawings of which are hereby also specifically incorporated herein by reference) describes the use of a stereoscopic imaging apparatus to view cells from multiple angles, for the reconstruction of a three-dimensional (3-D) map of the cell and accurate enumeration of FISH spots in images. The effectiveness of this technique is limited by the depth of field that can be achieved with the imaging system. If the depth of field of each detector is less than the depth of the cell, or at least, of the nucleus, the spatial resolution of the three-dimensional map produced by the technique will vary across the cell, and neighboring FISH spots in the image will blur into each other and be unresolved.

While the ImageStream™ flow imaging system represents a significant advance over conventional flow cytometry and standard microscopy, demanding applications, such as the quantization of FISH probed cells, require imaging capabilities closer to those achieved by confocal image stacking.

It would therefore be desirable to develop a flow imaging system suitable for high-resolution imagery (0.75 NA and 0.5 micron pixel size), which also exhibits an extended depth of field.

SUMMARY

This application specifically incorporates by reference the disclosures and drawings of each patent application and issued patent identified above as a related application.

The concepts disclosed herein enable the depth of field of an imaging system to be increased. Such techniques are particularly well suited for enabling flow imaging systems suitable for high-resolution imagery (0.75 NA and 0.5 micron pixel size) to achieve extended depth of field cellular images similar to those obtained using confocal image stacking. Because flow imaging systems can acquire image data much more rapidly than confocal microscopy, these techniques will facilitate the analysis of large cellular populations. The concepts disclosed herein further encompass imaging systems configured to achieve such extended depth of field imaging.

If the point spread function (PSF) of an imaging system is well-characterized, the known PSF can be used to improve the spatial resolution of imagery acquired with the imaging system by mathematically de-convolving the PSF from the imagery. In the case where object being imaged lies entirely within the focal plane, only a single image of the object need be acquired. If the object being imaged is extended in the Z axis, multiple images of the object must be acquired in different focal planes order to produce the resolution enhancement, due to uncertainty about the focal plane of origin of any given feature within a single image of an extended object. However, a single image of an extended object can be combined with PSF de-convolution to enhance focus quality (rather than resolution) if the PSF is intentionally modified such that it is invariant to focal position. The techniques disclosed herein are therefore based on manipulating an imaging system such that a point spread function (PSF) of the imaging system is substantially invariant over an extended depth of field. For example, where an unmodified high-resolution imaging system might exhibit a depth of field of about 1 micron, a modified version of the same imaging system might be characterized as having a PSF that is substantially invariant across a depth of field of about 10 microns. Such a substantially invariant PSF enables the imaging system to integrate light from different focal positions in object space, making the modified imaging system relatively insensitive to defocus. This property, in turn, enables de-convolution of the PSF to remove the spatial broadening and contrast loss inherent in the unprocessed image, thereby increasing image fidelity and creating an "in-focus" projected image of the entire cell. The concepts presented herein combine the above technique for extending depth of field with a means for greatly increasing detection sensitivity. The increased sensitivity is important to the practice of extended depth of field imaging, because the PSF modification tends to blur optical signals in the unprocessed imagery, thereby decreasing the signal to noise ratio. Further, the de-convolution process itself tends to amplify noise, reducing the effective signal to noise ratio in the resultant extended depth of field imagery, so increasing the signal intensity relative to the noise is a key feature of the present invention A key aspect of the concepts presented in the examples discussed herein is that a wave front of light from the object is deformed, such that light from different focal positions is collected. As long as the deformation process is well understood, processing of the imaging data collected from the deformed light can correct for errors introduced into the image data by the deformation process, while enabling the information corresponding to the different focal positions to be retained. Thus, after such corrective processing is applied, an image with an extended depth of field is obtained.

Thus, the following steps can be considered to be an overview of an exemplary process disclosed herein: providing an imaging system having a substantially invariant PSF (or modifying an imaging system to achieve a substantially invariant PSF), collecting image data from an object, and processing that image data to achieve an extended depth of field image. De-convolving the image (taking into account the modified PSF) enhances image contrast and reduces spatial broadening, thereby improving image quality.

The concepts disclosed herein encompass several different exemplary techniques for providing the substantially invariant PSF and the deformed wave front. As noted above, U.S. Pat. No. 6,583,865 describes a flow imaging system having a tilted image plane (either the detector being tilted or the flow path of the object relative to the detector is tilted). Several improvements to that configuration are disclosed herein, including the use of a flow cell having a tilted flow path. Significantly, such an approach does not simultaneously collect data from a plurality of different focal positions. Instead, as the object moves relative to the tilted image plane, the focal point of the imaging system moves to different focal planes in the object. A detector synchronized to the motion of the object must be employed (i.e., a time delay integration (TDI) detector), such that images of the object obtained at different positions (and at different times) are combined to achieve an extended depth of field image of the object. Rather than using such a tilted image plane, an optical element configured to deform the optical wave front of light from the image can be introduced into the imaging system between the object and the detector. One advantage to using an optical element to deform the optical wave front is that light is simultaneously collected from an EDF in the object. Thus, a synchronized detector is not required (although it may still be desirable to employ such a detector). Another advantage to using an optical element to deform the optical wave front is that the element may be conveniently inserted into or removed from the optical system. Different imaging applications may require more or less depth of field, and having a removable element allows the depth of field to be tailored to the different applications of the imaging system. A phase plate (an exemplary phase plate can be obtained from CDM Optics of Boulder Colo., marketed as a Wavefront Coded™ element) represents one type of optical element that can be used to deform the optical wave front. Yet another type of optical element will deform the wave front by introducing a spherical aberration into light from the object. A separate optical element (such as a cover slip) can be used to introduce spherical aberration, or an existing element in the flow imaging system (such as a flow cell or cuvette, or an objective lens with a correction collar) can be modified to introduce the spherical aberration. Where the optical element is a phase plate or wave front coded (WFC) element, such an optical element will be disposed in infinite space, otherwise known as aperture space (i.e., behind the objective lens). If the optical element introduces spherical aberration, such aberration is preferably induced before light is collected by the aperture of the imaging system (i.e., between the object or cell being imaged and the objective lens). Essentially, the unmodified imaging system (i.e., the imaging system without the distortion element) is configured to acquire an image of the object with a relatively narrow depth of field (for example, about 1 micron, understanding that such a value is intended to be exemplary, and not limiting). When the distortion element is introduced into the imaging system, the distortion element induces defocus in the light from the object, such that the relatively narrow depth of field is expanded (in an exemplary, but not limiting embodiment, the defocus extends about +/−7 microns beyond the original depth of field); however, such defocus "blurs" the extended depth of field (such blur generally includes both spatial broadening and a loss of contrast). Post image acquisition processing can minimize the blurring effects of the defocus induced by the distortion element, enabling an EDF image to be generated. Note that the PSF of the imaging system with the distortion element in place is used to facilitate the post image acquisition processing employed to reduce the effects of the defocus induced by the distortion element.

Another aspect of the concepts encompassed herein is directed to a flow imaging system configured to provide the above-described extended depth of field images. Such a flow imaging system will include an optical element to deform the wave front of light from the object while providing a substantially invariant PSF, a collection element to direct light from the object along an light path, an imaging lens configured to form an image from the collected light, a detector configured to detect the image and generate image data, and a processor configured to process the image data (i.e., to de-convolve the image data based on the invariant PSF) to produce an extended depth of field image of an object. In some exemplary embodiments, the imaging system includes a dispersion element that disperses the collected light before imaging, and in some exemplary embodiments, the detector is a TDI detector, configured to output image data based on a plurality of images of the object detected over time.

Referring to the ImageStream™ system noted above, the concepts encompassed herein can be applied to the ImageStream™ system, to enable extended depth of field imaging to be achieved. An ImageStream™ system modified for extended depth of field (EDF) image collection can provide for the collection of high-resolution imagery (0.75 NA and 0.5 micron pixel size) without the defocus associated with high NA optics. Such imagery will have a greatly extended depth of field (a proposed EDF ImageStream™ will achieve a depth of field of ten microns, which is approximately five times the current operating single focal plane depth of less than two microns), allowing for all image features within a 10 micron EDF to be clearly in focus. This technology will enable imaging of cellular components having fine structures that are in different focal planes (e.g., cytoplasmic proteins, such as actin, microtubules, and sub-cellular organelles (such as mitochondria), cellular micro-domains (e.g., membrane caps, lipid rafts, protein co-localization, and signal transduction), and fluorescent in-situ hybridization spot counting. Significantly, post-processing of the imagery minimizes the effects of defocus by bringing the entire cell into focus at the same time. Unlike confocal image stacking techniques, this new methodology and apparatus will operate at hundreds of cells per second, allowing tens of thousands of cell images to be collected for quantitative analysis in several minutes.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 1A:
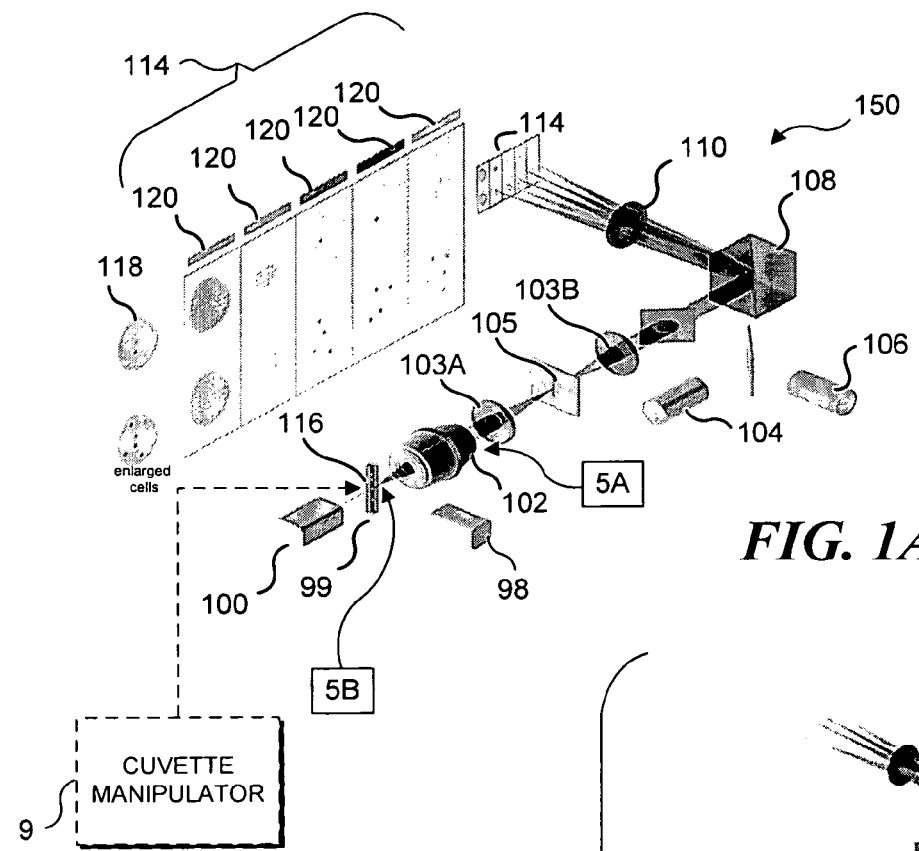
FIG. 1A is a schematic illustration of an exemplary flow imaging system for implementing the concepts disclosed herein.
Figure 5:
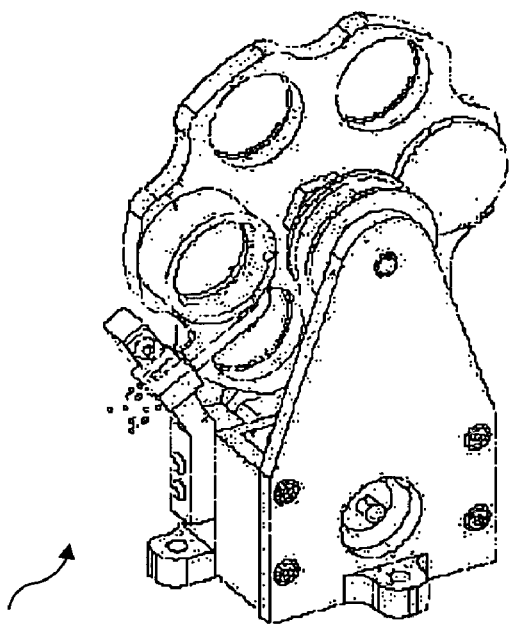
Figure 6:
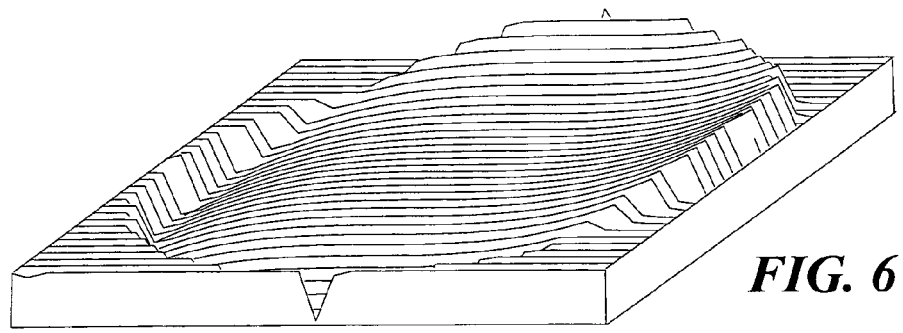
Figure 7:
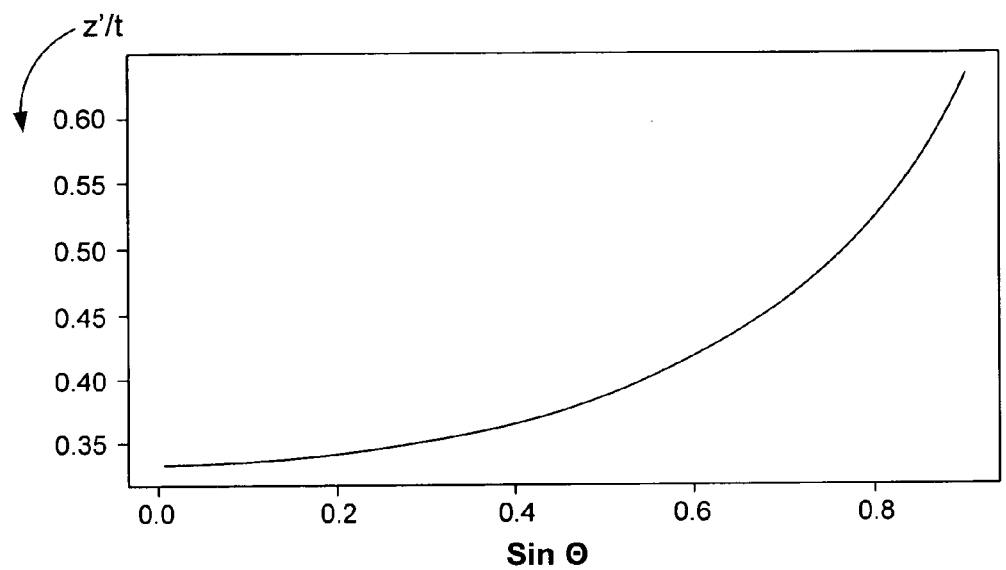
Figure 8:
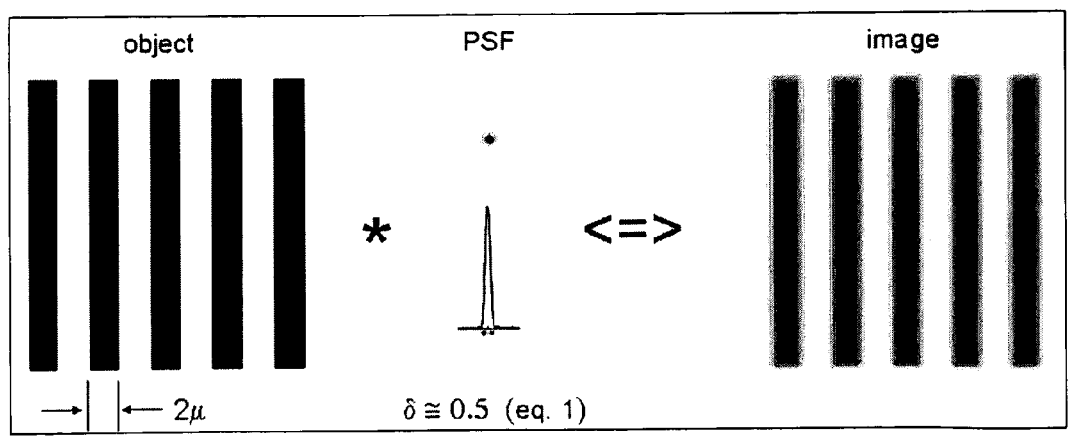
Figure 9:
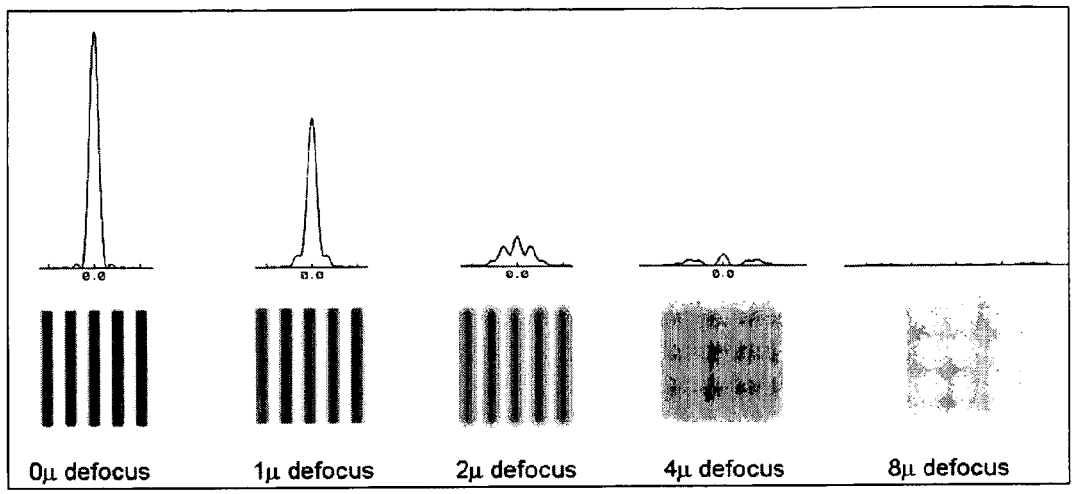
Figure 10A:
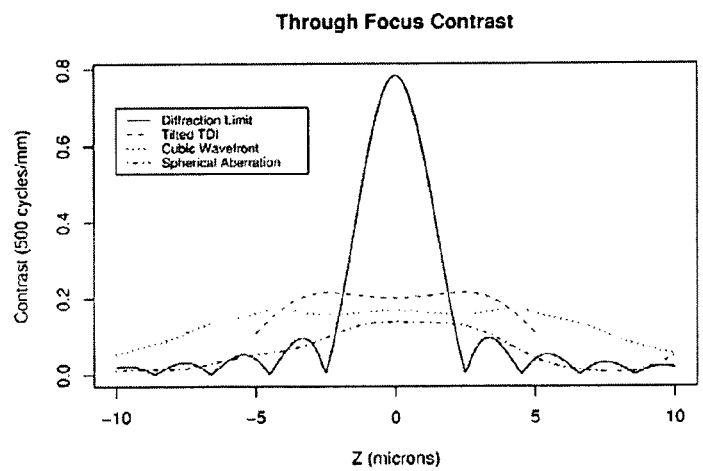
Figure 10B:
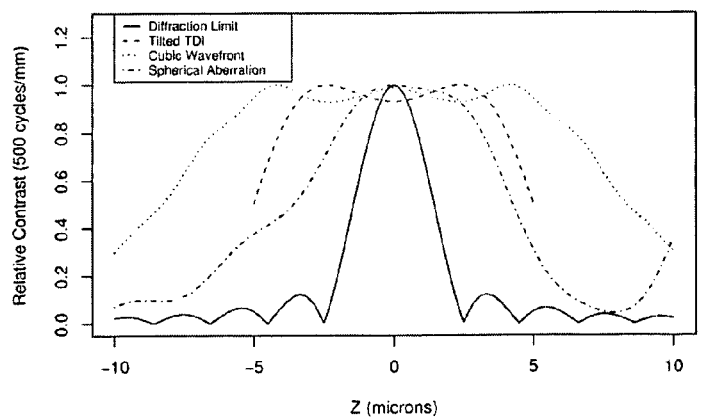
Figure 11A:
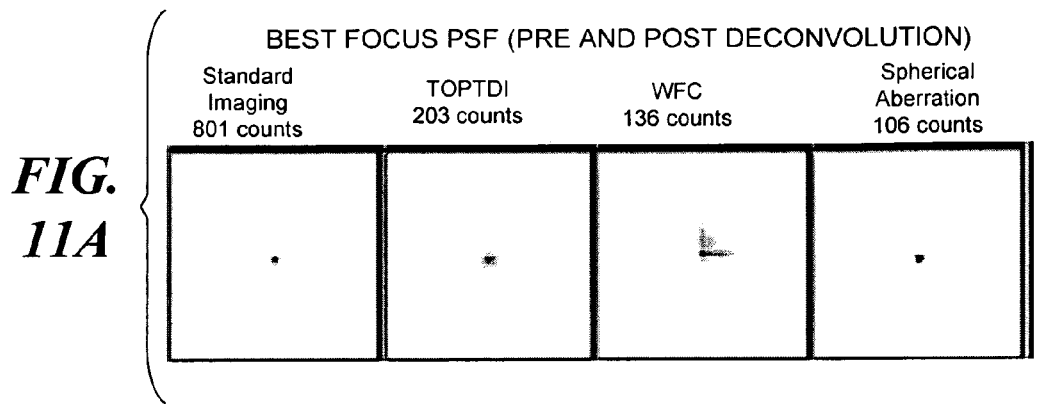
Figure 11B:
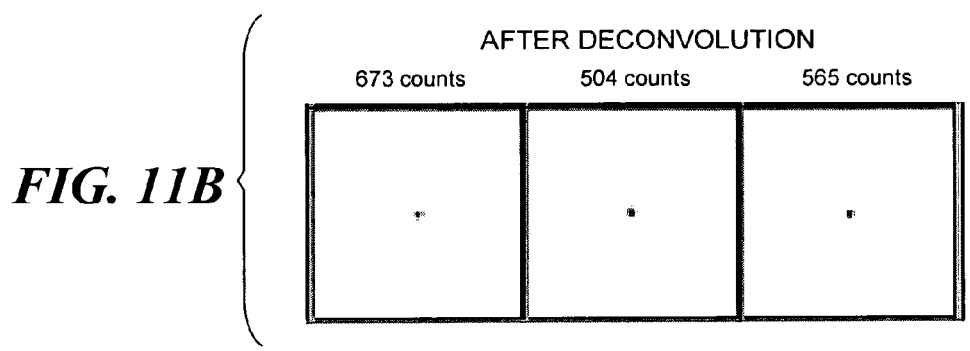
Figure 12A:
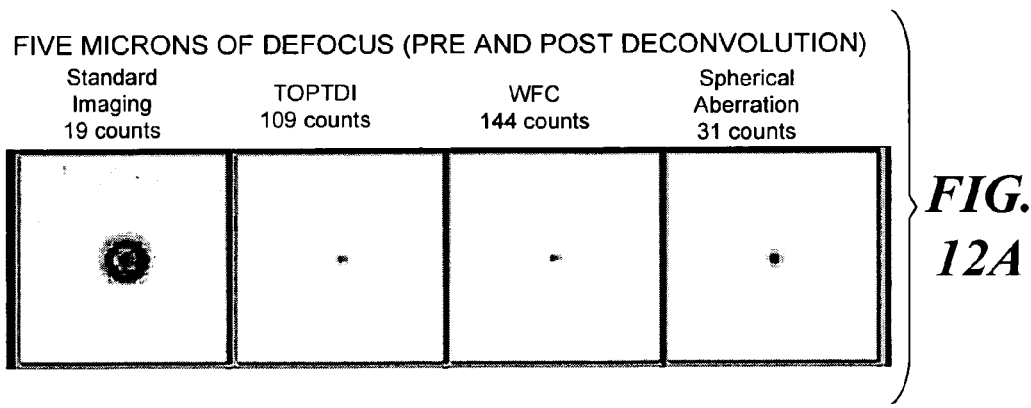
Figure 12B:
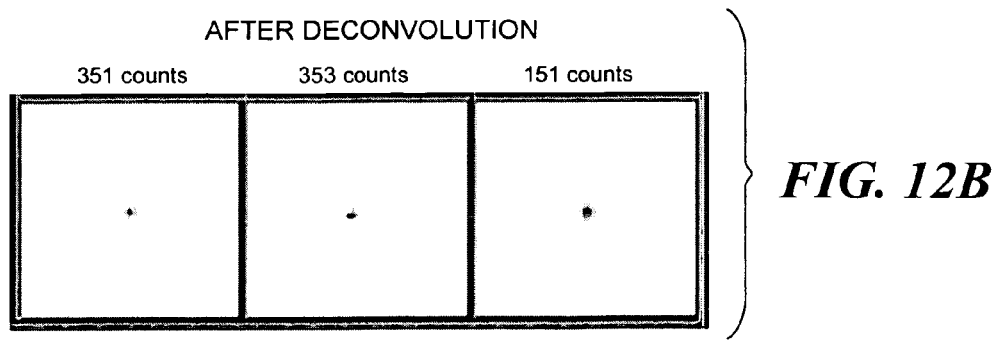
Figure 13B:
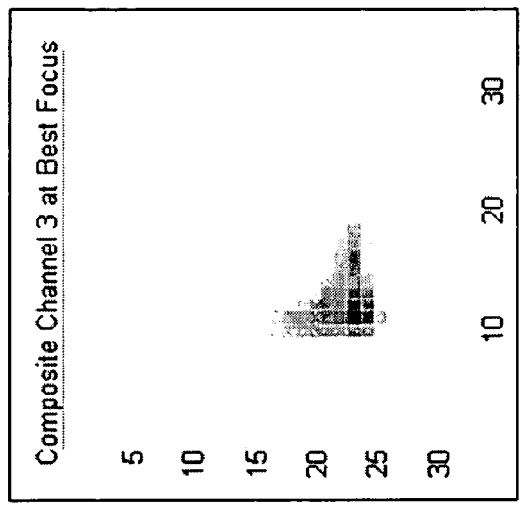
Figure 13A:
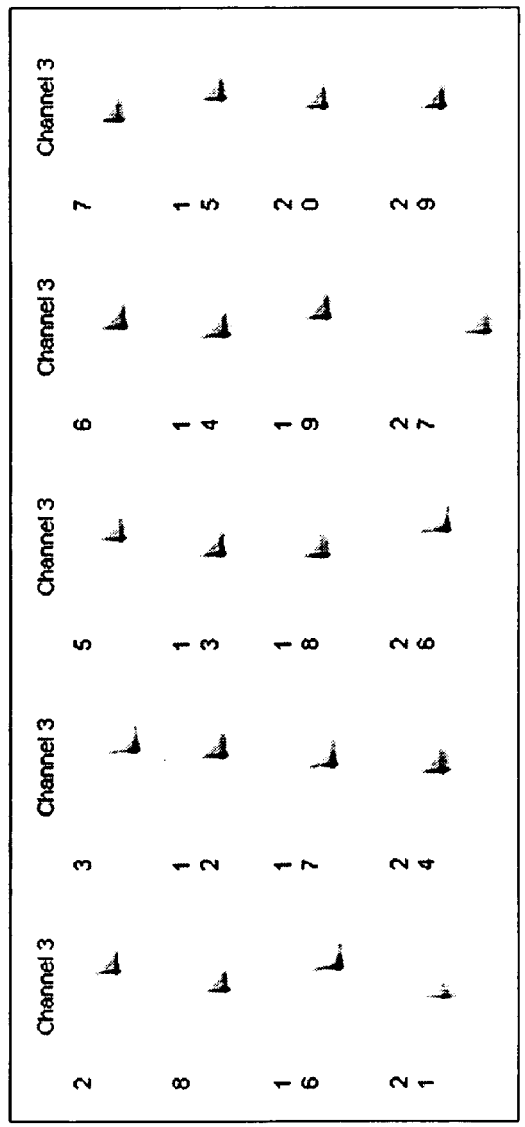
Figure 17A:
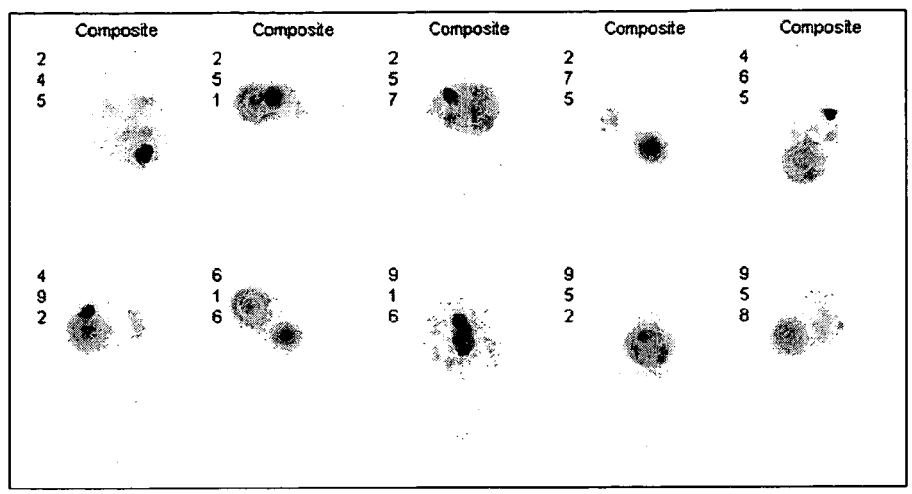
Figure 17B:
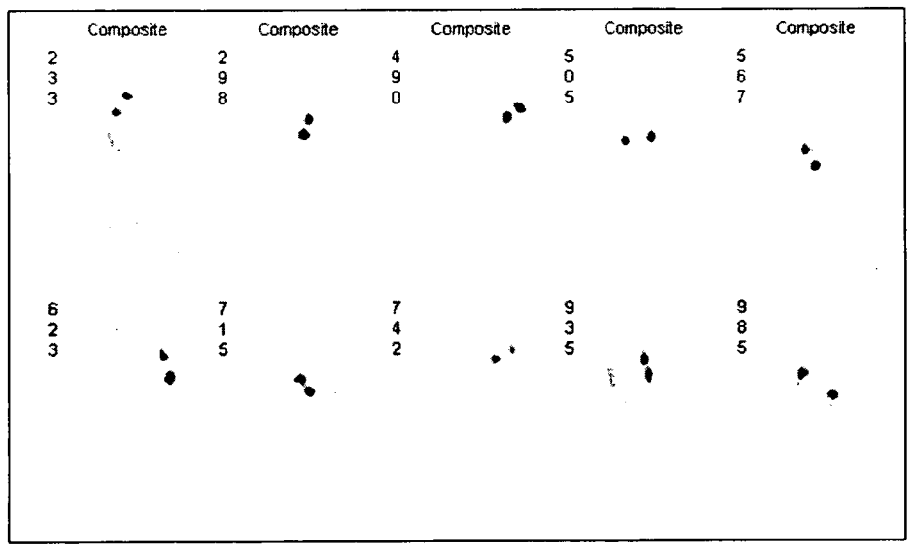
Figure 20:
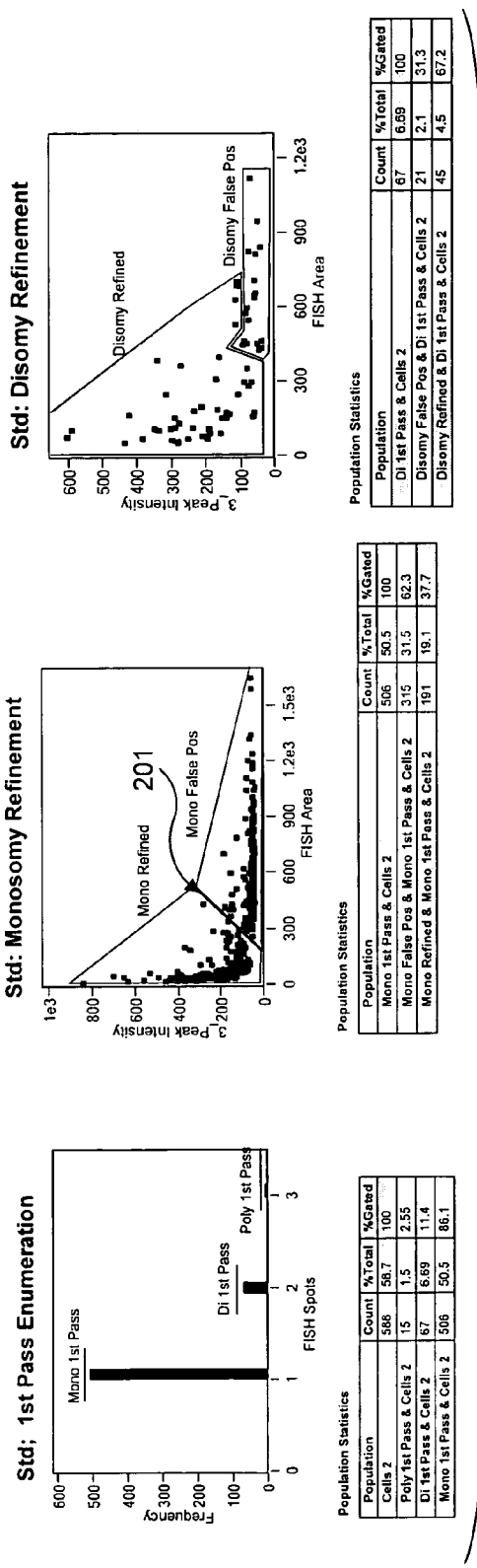
Figure 21:
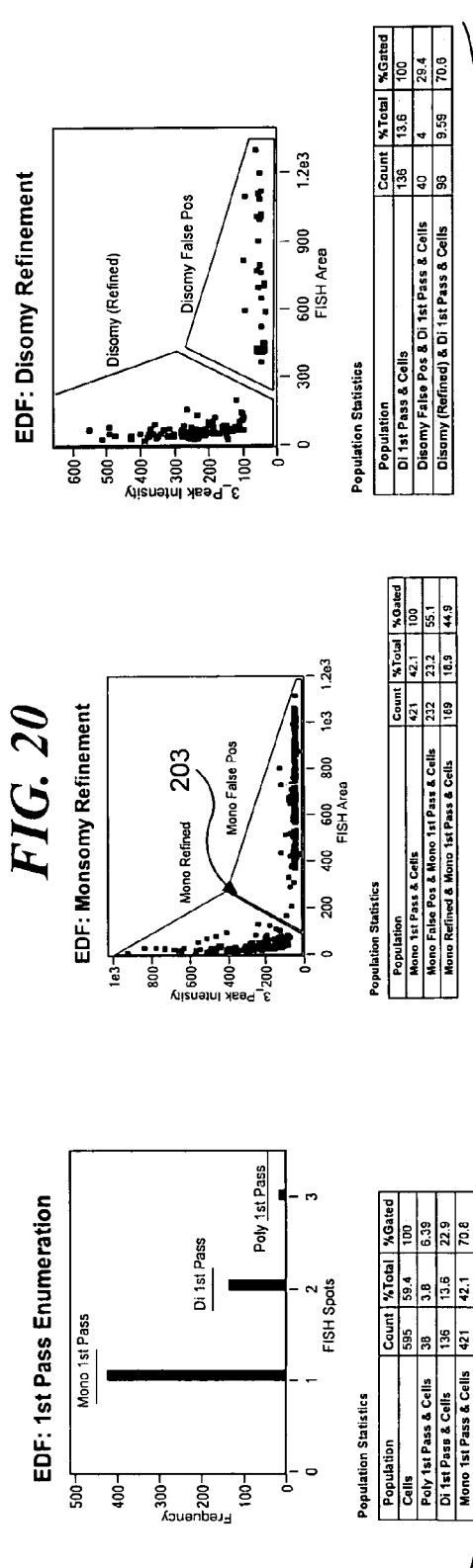
Figure 22A:
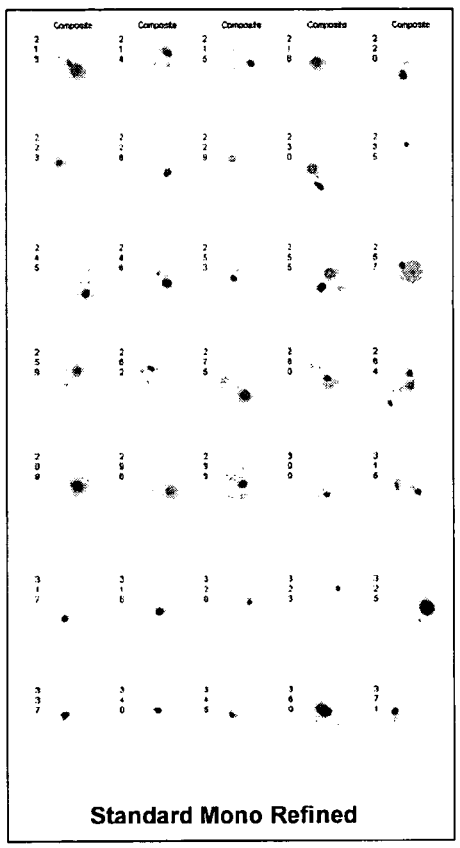
Figure 23A:
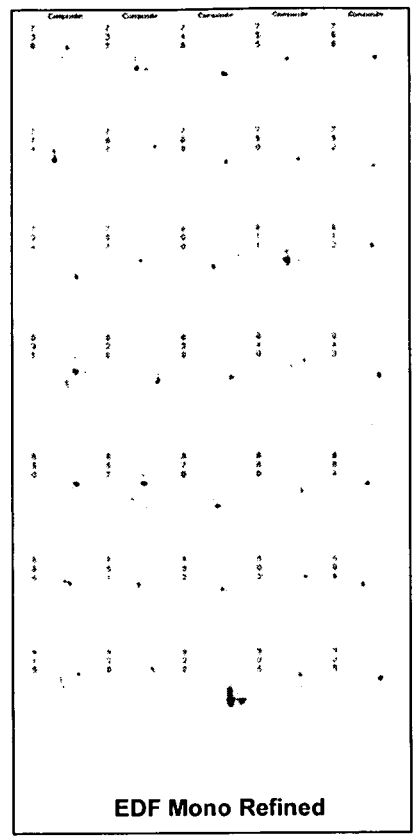
Figure 22B:
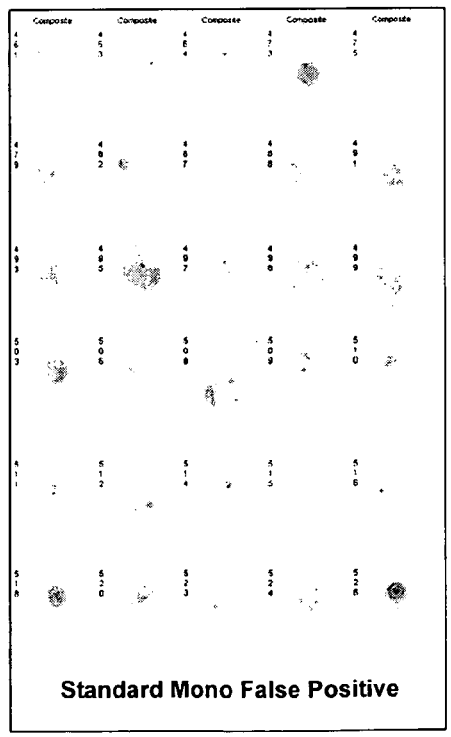
Figure 23B:
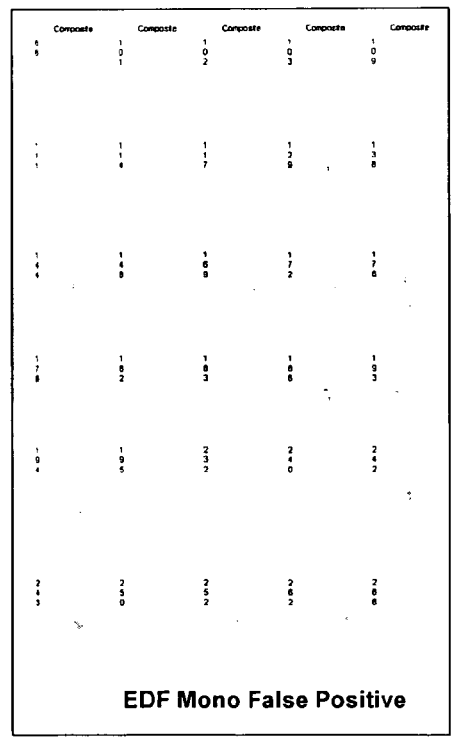
Figure 22C:
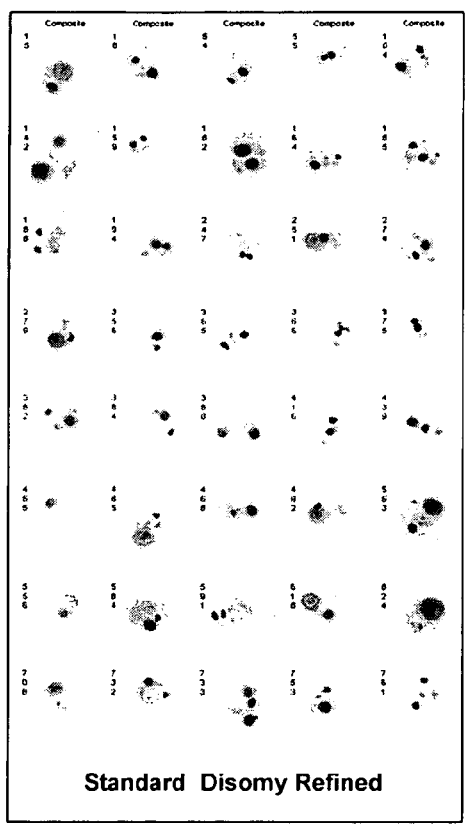
Figure 23C:
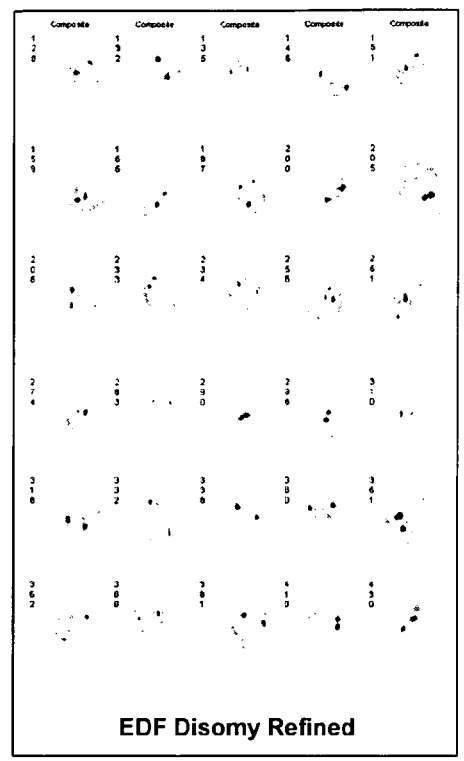
Figure 22D:
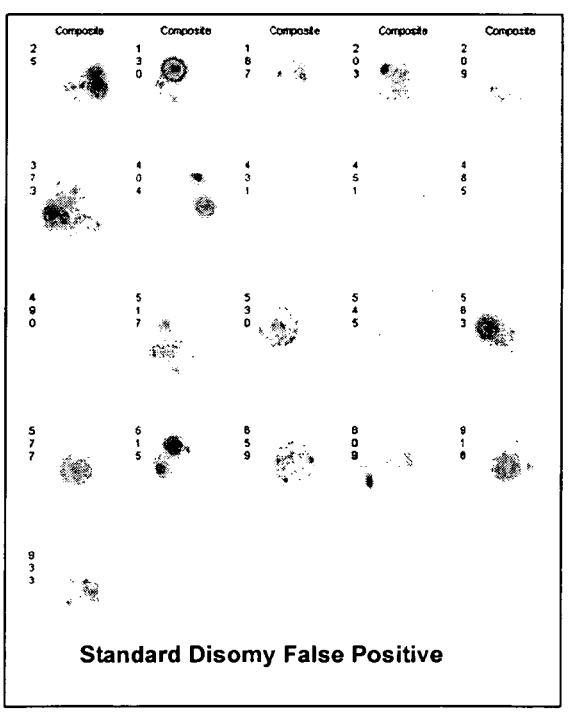
Figure 23D:
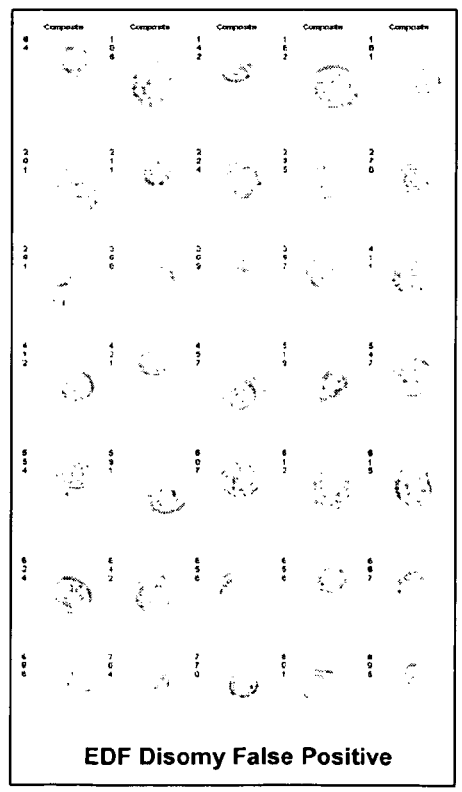

FIG. 5 schematically illustrates a filter wheel for selectively positioning an wave front distortion element in a light path of a flow imaging system, such that the imaging system can be used for both EDF imaging and normal imaging, depending on the position of the filter wheel relative to the light path;

FIG. 6 illustrates a three-dimensional (3-D) contour of an exemplary optical element configured to deform the optical wave front of light from an object;

FIG. 7 graphically illustrates the fractional focal offset as a function of transmission angle due to a glass parallel plate, representing another type of optical element that can be used to intentionally deform light from the object;

FIG. 8 schematically illustrates how the PSF of an imaging system affects the quality of an image generated by the imaging system;

FIG. 9 schematically illustrates the effect that varying degrees of defocus have on an image acquired using a standard non-extended depth of field imaging method;

FIG. 10A graphically illustrates an absolute comparison of through focus modulation transfer functions, at half the Nyquist frequency, of a standard non-extended depth of field imaging method and a plurality of extended depth of field (EDF) imaging methods, as disclosed herein, the EDF methods including an exemplary Wave Front Coded (WFC) EDF method, an exemplary Spherical Aberration EDF method, and an exemplary Tilted Object Plane Time Delay Integration (TOPTDI) EDF method;

FIG. 10B graphically illustrates a normalized comparison of modulation transfer functions of a standard non-extended depth of field imaging method (diffraction limited) and the WFC EDF method, the Spherical Aberration EDF method, and the TOPTDI EDF method;

FIG. 11A illustrates the best focus imagery obtained using the exemplary imaging system of FIG. 1A, for both standard imaging and EDF imaging, before processing the image data to correct for errors introduced by the wave front deformation;

FIG. 11B illustrates the best focus imagery obtained using the exemplary imaging system of FIG. 1A, for various EDF techniques, after de-convolution;

FIG. 12A illustrates the imagery 5 microns away from the best focus obtained using the exemplary imaging system of FIG. 1A, for both standard imaging and EDF imaging, before processing the image data to correct for errors introduced by the wave front deformation;

FIG. 12B illustrates the imagery 5 microns away from the best focus obtained using the exemplary imaging system of FIG. 1A, for various EDF techniques, after de-convolution;

FIG. 13A illustrates a sampling of PSF imagery collected using the exemplary imaging system of FIG. 1A, modified to implement WFC EDF imaging (modified by introducing a phase plate in infinite space);

FIG. 13B illustrates an exemplary de-convolution kernel;

Figures 14A, 14B:
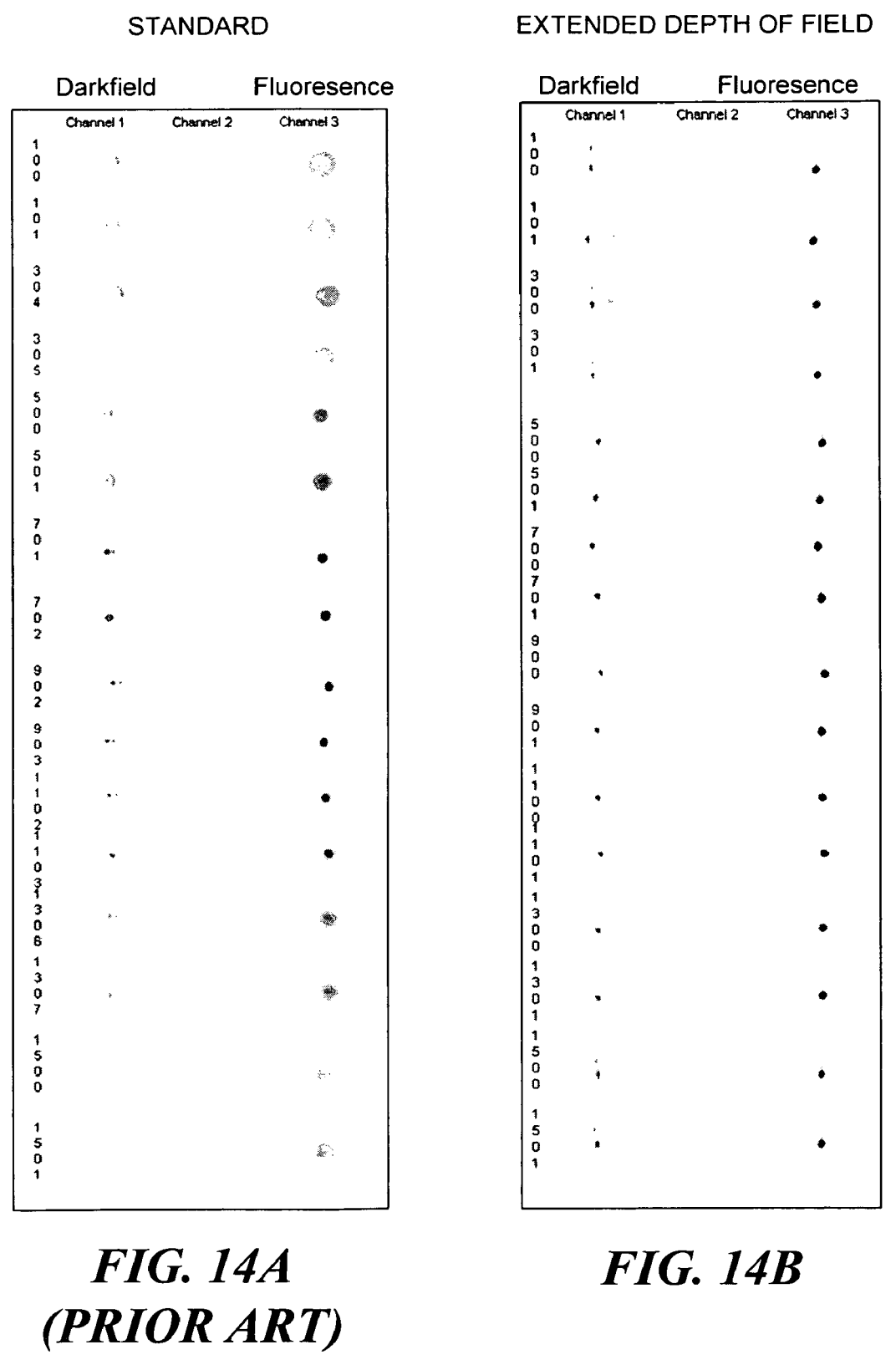

FIG. 14A illustrates the imagery collected using the exemplary imaging system of FIG. 1A over a 16 micron focus pan for standard imaging (i.e., not EDF imaging);

FIG. 14B illustrates the imagery collected using the exemplary imaging system of FIG. 1A modified for WFC EDF over a 16 micron focus pan;

FIG. 15A illustrates peak pixel intensity versus object number for image data collected by the exemplary imaging system of FIG. 1A operating in a standard mode (i.e., not EDF imaging)) during a step-wise focus pan in which approximately 200 objects were imaged at each of nine focus positions;

FIG. 15B illustrates area versus object number for image data collected by the exemplary imaging system of FIG. 1A operating in a standard mode (i.e., not EDF imaging) during a step-wise focus pan in which approximately 200 objects were imaged at each of nine focus positions;

FIG. 16A illustrates peak pixel intensity versus object number for image data collected by the exemplary imaging system of FIG. 1A operating in an EDF mode) during a step-wise focus pan in which approximately 200 objects were imaged at each of nine focus positions;

FIG. 16B illustrates area versus object number for image data collected by the exemplary imaging system of FIG. 1A operating in an EDF mode) during a step-wise focus pan in which approximately 200 objects were imaged at each of nine focus positions;

FIG. 17A illustrates FISH imagery of cells with disomy for chromosome Y collected by the exemplary imaging system of FIG. 1A operating in a standard mode (i.e., not EDF imaging);

FIG. 17B illustrates FISH imagery of cells with disomy for chromosome Y collected by the exemplary imaging system of FIG. 1A operating in an EDF mode;

FIG. 18 graphically illustrates how EDF data collected using the exemplary imaging system of FIG. 1A operating in EDF mode can be used to discriminate single cells from debris or cell clusters prior to classifying and enumerating chromosomes;

FIG. 19A graphically illustrates a gray-scale fluorescence image prior to segmentation;

FIG. 19B graphically illustrates a segmentation mask to isolate areas of local maxima after initial segmentation;

FIG. 19C graphically illustrates a segmentation mask to isolate areas of local maxima after morphology segmentation;

FIG. 20 graphically illustrates an analysis of cellular images obtained using the exemplary imaging system of FIG. 1A operating in a standard mode (i.e., not EDF imaging);

FIG. 21 graphically illustrates an analysis of cellular images obtained using the exemplary imaging system of FIG. 1A operating in an EDF mode;

FIGS. 22A-22D illustrate randomly selected cell imagery obtained using the exemplary imaging system of FIG. 1A operating in a standard mode (i.e., not EDF imaging) and corresponding to "Monosomy Refinement" gates (FIG. 22A), Monosomy false positive events (FIG. 22B), "Disomy Refinement" gates (FIG. 22C), and "Disomy false positive events (FIG. 22D); and FIGS. 23A-23D illustrate randomly selected cell imagery obtained using the exemplary imaging system of FIG. 1A operating in an EDF mode and corresponding to "Monosomy Refinement" gates (FIG. 23A), "Monosomy false positive events" (FIG. 23B), "Disomy Refinement" gates (FIG. 23C), and "Disomy false positive events" (FIG. 23D).

Figure 4:
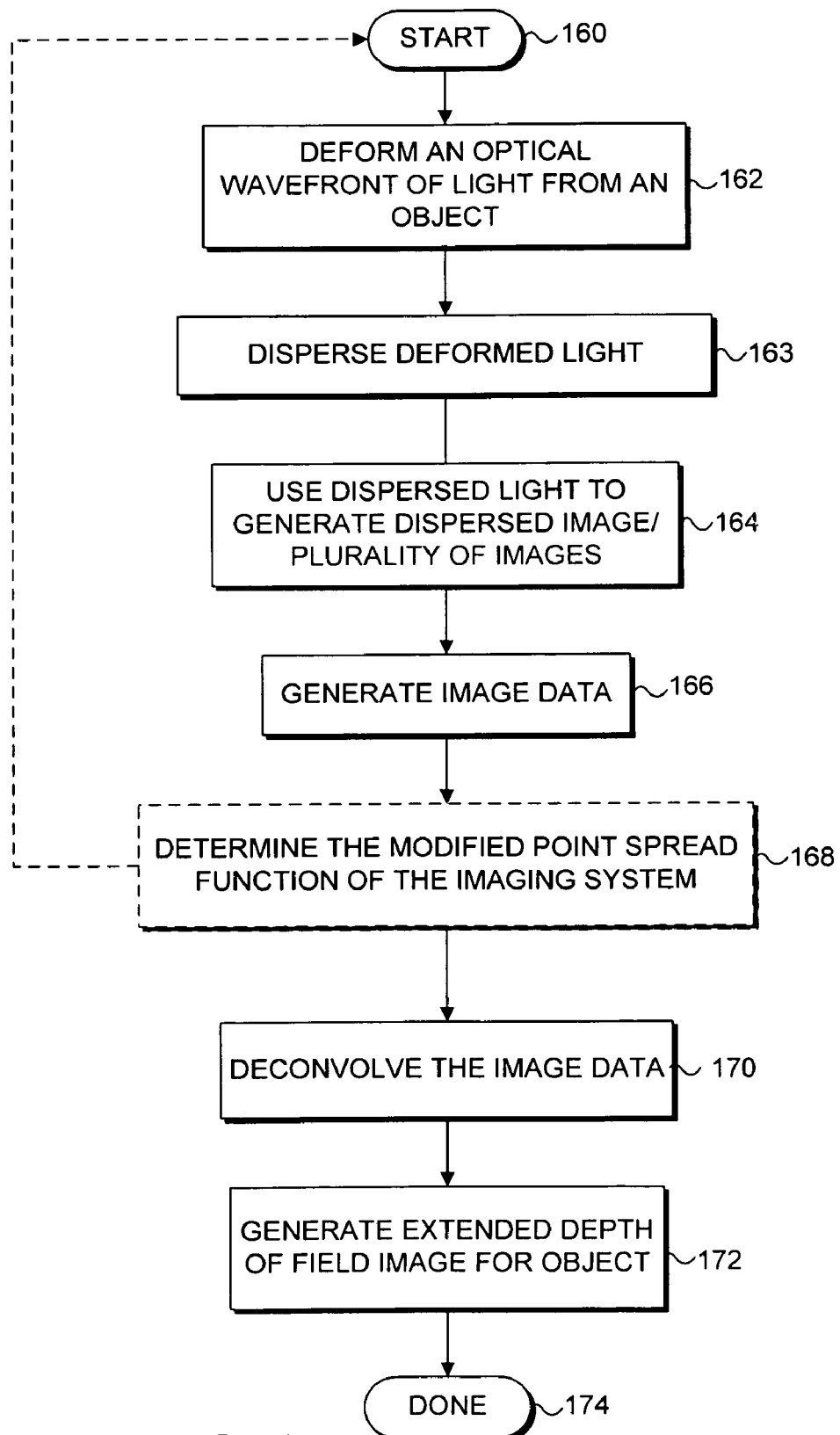
FIG. 4 is a block diagram schematically illustrating a method of providing extended depth of field imagery for an object.
Figure 24:
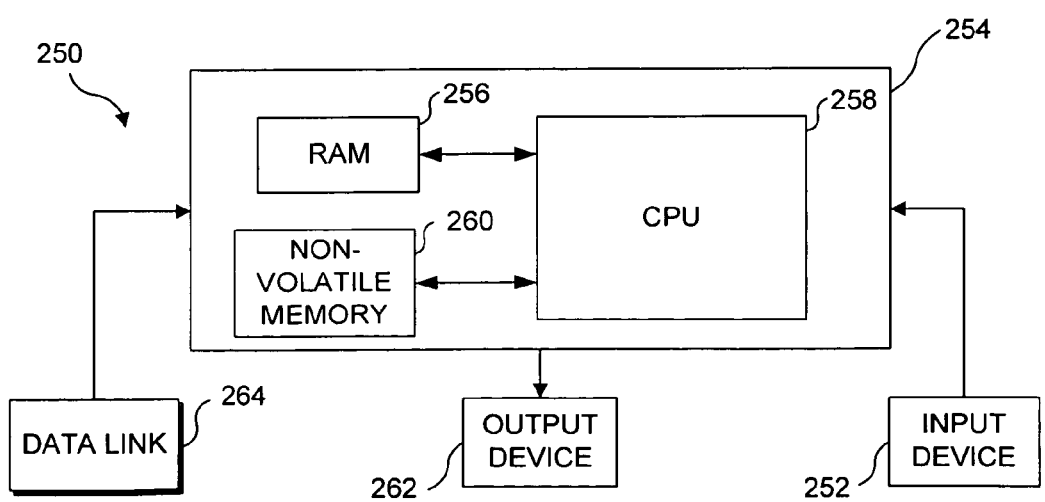

FIG. 24 schematically illustrates an exemplary computing system used to implement the method steps of FIG. 4.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

The concepts disclosed herein encompass a method of adding extended depth of field capability to a flow imaging system configured for high-resolution imagery (exemplary, but not limiting parameters include 0.75 NA and 0.5 micron pixel size). It thus should be recognized that the term "standard image" or "standard imaging" refers to use of an exemplary flow imaging system (described in detail below) that has not been modified for EDF imaging. Such a flow imaging system can combine the speed, sample handling, and cell sorting capabilities of flow cytometry with the imagery, sensitivity, and resolution of multimode imagery with an extended depth of field in order to provide a comprehensive feature set to more effectively eliminate artifacts and allow for the complex analysis of the location, distribution, and translocation of biomarkers. Standard, non-confocal methods of image collection are hindered by extended depth of field limitations. The EDF capability described herein is a result of modifying an exemplary flow imaging system with an element in aperture space to alter the wave front in a deterministic way. The combination of a modified wave front and post-processing of the imagery helps to mitigate the spatial resolution loss and blurring associated with defocus. The result is a 2-D projection of the 3-D cell for each of six multimode images (it being understood that the use of six images are exemplary, and not limiting on the technique) acquired at rates 100 to 1000 times faster than confocal image stacking techniques. With the extended depth of field enhancement disclosed herein, micron-level spatial resolution can be maintained over the entire cell so that cellular structures and probes lying outside the plane of best focus can be analyzed with greater accuracy, as demonstrated with empirical FISH probe image data discussed in detail below.

More specifically, there are at least four applications in which such EDF imagery from flow imaging systems can be beneficially employed, including: (1) Cell Activation, such as transcription factor NF-eB nuclear translocation; (2) Mechanisms of Monoclonal Antibody Drug Action, co-localization and compartmentalization; (3) Apoptosis Analysis: differential rates of apoptosis in heterogeneous cell samples; and, (4) Morphologic cell classification, the identification of cells in blood and bone marrow.

Figure 3:
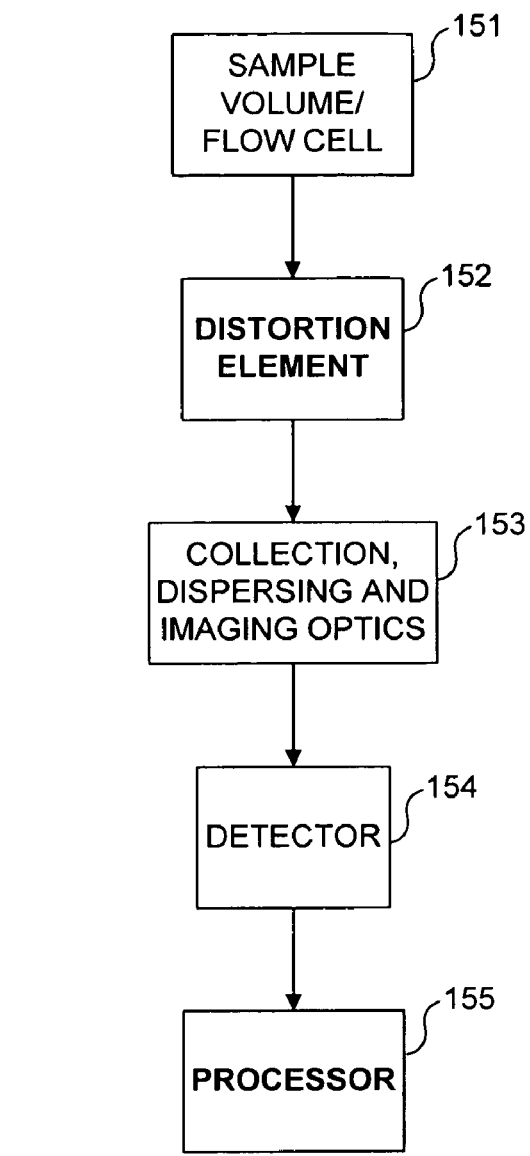
FIG. 3 is a block diagram schematically illustrating the basic components of an exemplary flow imaging system suitable for implementing the concepts disclosed herein.

Before discussing the steps employed in one exemplary embodiment for implementing the present novel approach, it will be beneficial to review an exemplary flow imaging system 150 that can be used to execute this method. FIG. 1A illustrates the key components of an optical system employed to project light from objects in flow onto a detector that employs an exemplary readout for any type of small object (although imaging cells represent an exemplary application). Objects are hydrodynamically focused into a single-file line in a fluidic system (not separately shown), forming a tall but narrow field of view. This method enables the lateral dimension of the detector to be used for signal decomposition. FIG. 3 is a block diagram showing the major components of exemplary flow imaging system 150. A key component is a distortion element 152, which is used to distort the wave front of the light collected from an object, in a predictable and largely reversible fashion, while expanding the field of view. Referring to FIG. 3, the major components of a multi-mode EDF flow imaging system include a flow cell or cuvette 151 into which object (such as cells) to be imaged are directed, an optical distortion element 152 to introduce a well-characterized distortion of light received from the object (such that the PSF of the imaging system is substantially invariant over a range of focal planes), collection, dispersing, and imaging optical elements 153 (to enable the multi-mode imaging such as shown in FIG. 1A to be achieved), a detector 154 for generating raw image data (preferably, a TDI detector, although other imaging detectors can alternatively be employed, i.e., non-TDI imaging detectors can also be used), and a processor 155 for processing the image data, to enhance the image data and at least partially correct for the distortions introduced by the distortion element. Such processing can comprise a de-convolution that reduces spatial broadening and enhances contrast. It should be recognized that such processing can be implemented using hardware (e.g., a custom processing circuit or an application specific integrated circuit (ASIC)), or a combination of hardware and software (e.g., a software-driven processor, such as is typically used in a computing device, a personal computer being one well-known example thereof). It should further be recognized that the distortion element may be physically located outside of the aperture of the imaging system (i.e. between the flow cell and the imaging objective in the case of the spherical aberration technique), in aperture space after the imaging objective (in the case of the WFC technique), or may be effected within the imaging objective itself by adjustment of an aberration correction collar.

Referring now to FIG. 1A, object(s) 99 are hydrodynamically focused in a flow of fluid directed into a flow cuvette 116 and illuminated from one or more sides using light sources 98 and 100. Light is collected from the objects with a high NA objective 102, and the light that is collected is directed along a light path including lenses 103A and 103B, and a slit 105. A fraction of this collected light is transmitted to an auto-focus subsystem 104 and to a velocity detection system 106. It should be noted that in connection with a velocity detection system 106 that uses a TDI, it is important to ensure the data signal produced by the detection system, which is integrated over time to increase the signal-to-noise ratio, is properly synchronized with the flow of objects through the imaging system. In the context of an exemplary implementation, the objects are fluorescently labeled beads or fluorescently labeled cells. The extended depth of field capability afforded by the present exemplary technique disclosed herein is particularly useful in automated chromosome enumeration via FISH probing of Jurkat cells, although such use is intended to be exemplary, rather than limiting on the application of this technique.

Either an optical distortion element 5A is disposed between the objects being imaged and the collection lens, or an optical distortion element 5B is disposed in infinite space (that is, at the objective aperture or at a conjugate image of the aperture at a subsequent location in the optical system, but before the detector). Alternatively, optical distortion may be introduced via adjustment of a correction collar on an adjustable implementation of objective lens 102. Only one means of introducing optical distortion is required. The function of the optical distortion is to change the light from the object to achieve a PSF that is substantially invariant across an EDF, such that negative effects of the distortion produced by the element can subsequently be removed by signal processing, to yield an EDF image.

Yet another technique that can be used to introduce optical distortion into light from the object is to use a cuvette/flow cell having different optical thicknesses at different locations, such that imaging through the different locations of the cuvette induces different degrees of wave front deformation. For example, different faces of the cuvette can induce different levels of distortion, with one or more faces introducing no intentional distortion/deformation, with other faces configured to intentionally deform the optical wave front of light from the object. Moving the cuvette relative to the imaging optical enables the deformation to be selectively induced. An optional cuvette manipulator 9 for manipulating the position of the cuvette relative to the optical system is shown in FIG. 1A. Where different faces of the cuvette induce different levels of deformation, such means will generally rotate the cuvette. It should also be recognized that a single face of a cuvette can induce different levels of deformation at different locations, such that translating the cuvette linearly can induce different levels of deformation. In such an embodiment, manipulator 9 will be configured to translate the cuvette linearly. Those of ordinary skill in the art will recognize that many different structural configurations can be used to implement manipulator 9, such as stepper motors, linear actuators, hydraulics, powered hinges, powered linkages, and others. The specific configuration is not critical, so long as manipulation of the cuvette does not introduce additional optical errors beyond the intentional deformation, thus the specified structures for manipulator 9 should be considered exemplary, rather than limiting.

The majority of the light is passed to a spectral decomposition element 108, which employs a fan-configuration of dichroic mirrors 110 to direct different spectral bands laterally onto different regions of a TDI detector 114. Thus, the imaging system is able to decompose the image of a single object 118 into multiple sub-images 120 across detector 114, each sub-image corresponding to a different spectral component. In this view, detector 114 has been enlarged and is shown separately to highlight its elements.

Figure 1B:
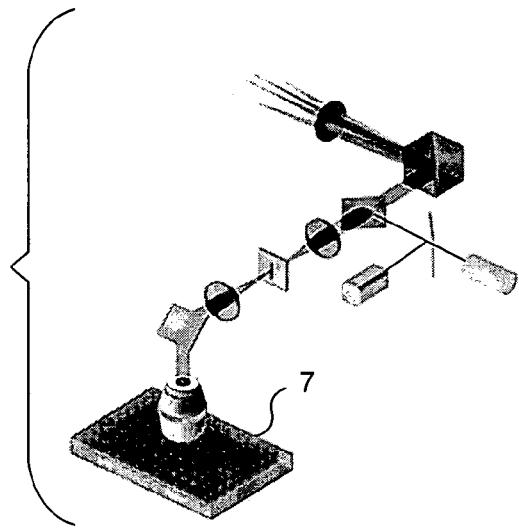
FIG. 1B is a schematic illustration of an exemplary imaging system for implementing the concepts disclosed herein, wherein the objected to be imaged are disposed on a plate or slide.

Spectral decomposition greatly facilitates the location, identification, and quantification of different fluorescence-labeled biomolecules within a cell by isolating probe signals from each other, and from background auto fluorescence. Spectral decomposition also enables simultaneous multimode imaging (brightfield, darkfield, etc.) using band-limited light in channels separate from those used for fluorescence imaging. FIG. 1A illustrates an exemplary flow-based embodiment of flow imaging system 150. However, it should be recognized that such an imaging system can be configured to collect images of objects on a plate or slide 7, where the plate/slide moves relative to the imaging system, instead of the flow-based embodiment, as indicated in FIG. 1B.

It should be recognized that other elements (such as a prism or a filter stack) could be similarly employed to spectrally disperse the light, and the dichroic mirrors simply represent an exemplary implementation. Flow imaging system 150 can employ a prism (not shown) or a grating oriented to disperse light laterally with regard to the axis of flow prior to the final focusing optics, for spectral analysis of each object's intrinsic fluorescence. In yet another exemplary embodiment of a suitable flow imaging system that is contemplated (but not shown), a cylindrical final focusing lens can be employed to image a Fourier plane on the detector in the cross-flow axis, enabling analysis of the light scatter angle. These techniques for multi-spectral imaging, flow spectroscopy, and Fourier plane scatter angle analysis can be employed simultaneously by splitting the collected light into separate collection paths, with appropriate optics in each light path. For enhanced morphology or to analyze forward scatter light, a second imaging objective and collection train can be used to image the particles through an orthogonal facet of the flow cuvette 116, thereby viewing the objects in stereoscopic perspective with no loss of speed or sensitivity.

To analyze the collected imagery, a software based image analysis program can be employed. One example of suitable image analysis software is the IDEAS™ package (available from Amnis Corporation, Seattle, Wash.). The IDEAS™ software package evaluates over 200 quantitative features for every cell, including multiple morphologic and fluorescence intensity measurements, which can be used to define and characterize cell populations. The IDEAS™ software package enables the user to define biologically relevant cell subpopulations, and analyze subpopulations using standard cytometry analyses, such as gating and backgating. It should be understood, however, that other image analysis methods or software packages can be employed to apply the concepts disclosed herein, and the IDEAS™ image analysis software package is intended to be merely one example of a suitable software for this purpose, rather than limiting on the concepts disclosed herein.

Figure 1C:
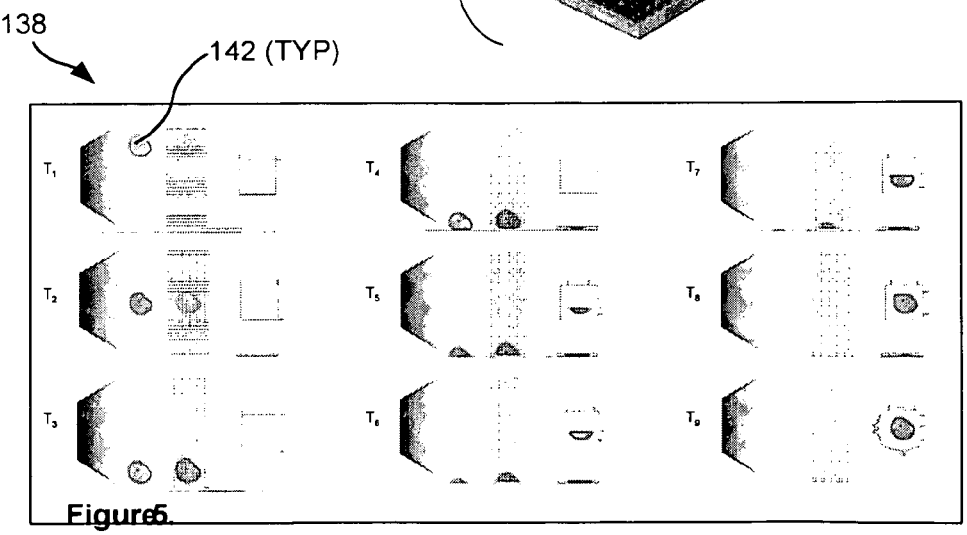
FIG. 1C is a schematic illustration of a readout provided by a TDI detector employed in an exemplary flow imaging system used in accord with the concepts disclosed herein.

Turning now to FIG. 1C, detector 114 of the exemplary flow imaging system shown in FIG. 1A is implemented using a TDI that performs high throughput imaging with high sensitivity. As shown in an exemplary readout 138, the image on the TDI detector is read out one row of pixels at a time from the bottom of the detector. After each row is read out, the signals in the remaining detector pixels are shifted down by one row. The readout/shift process repeats continuously, causing latent image 142 to translate down the detector during readout (note the movement of latent image 142 through frames T1-T6). If the readout rate of the TDI detector is matched to the velocity of the object being imaged, the image does not blur as it moves down the TDI detector. In effect, the TDI detector electronically "pans" the rate at which rows are read out to track the motion of an object being imaged. To provide optimum results for this technique, it is important to accurately measure the velocity of the objects being imaged and to employ that measurement in feedback control of the TDI readout rate. Thus, accurate velocity detection for objects moving in flow enables the TDI imaging to be implemented properly.

One primary advantage of TDI detection over other methods is the greatly increased image integration period it provides. An exemplary flow imaging system used in connection with the present invention includes a TDI detector that has 512 rows of pixels, provides a commensurate 512× increase in signal integration time. This increase enables the detection of even faint fluorescent probes within cell images and intrinsic auto fluorescence of cells acquired at a high-throughput.

Furthermore, the use of a TDI detector increases measured signal intensities up to a thousand fold, representing over a 30 fold improvement in the signal-to-noise ratio compared to other methods disclosed in the prior art. This increased signal intensity enables individual particles to be optically addressed, providing high-resolution measurement of either scattered spectral intensity of white light or scattered angular analysis of monochromatic light of selected wavelengths.

Exemplary flow imaging system 150 can be configured for multi-spectral imaging and can operate with, for example, six spectral channels: DAPI fluorescence (400-460 nm), Darkfield (460-500 nm), FITC fluorescence (500-560 nm), PE fluorescence (560-595 nm), Brightfield (595-650 nm), and Deep Red (650-700 nm). The TDI detector can provide 10 bit digital resolution per pixel. The NA of the exemplary imaging system is typically about 0.75, with a pixel size of approximately 0.5 microns. However, those skilled in the art will recognize that this flow imaging system is neither limited to six spectral channels nor limited to either the stated NA, or pixel size and resolution.

While the elimination of focus variation in a 2-D projection of a cell will likely be beneficial in many applications, it may be limiting in others, such as co-localization assays. This possibility was a key consideration in the utilization of a phase plate for the WFC EDF methodology, because the WFC EDF method can be implemented to provide different levels of distortion, or disabled completely, by removing or substituting optical elements in the system's aperture plane.

Figure 2:
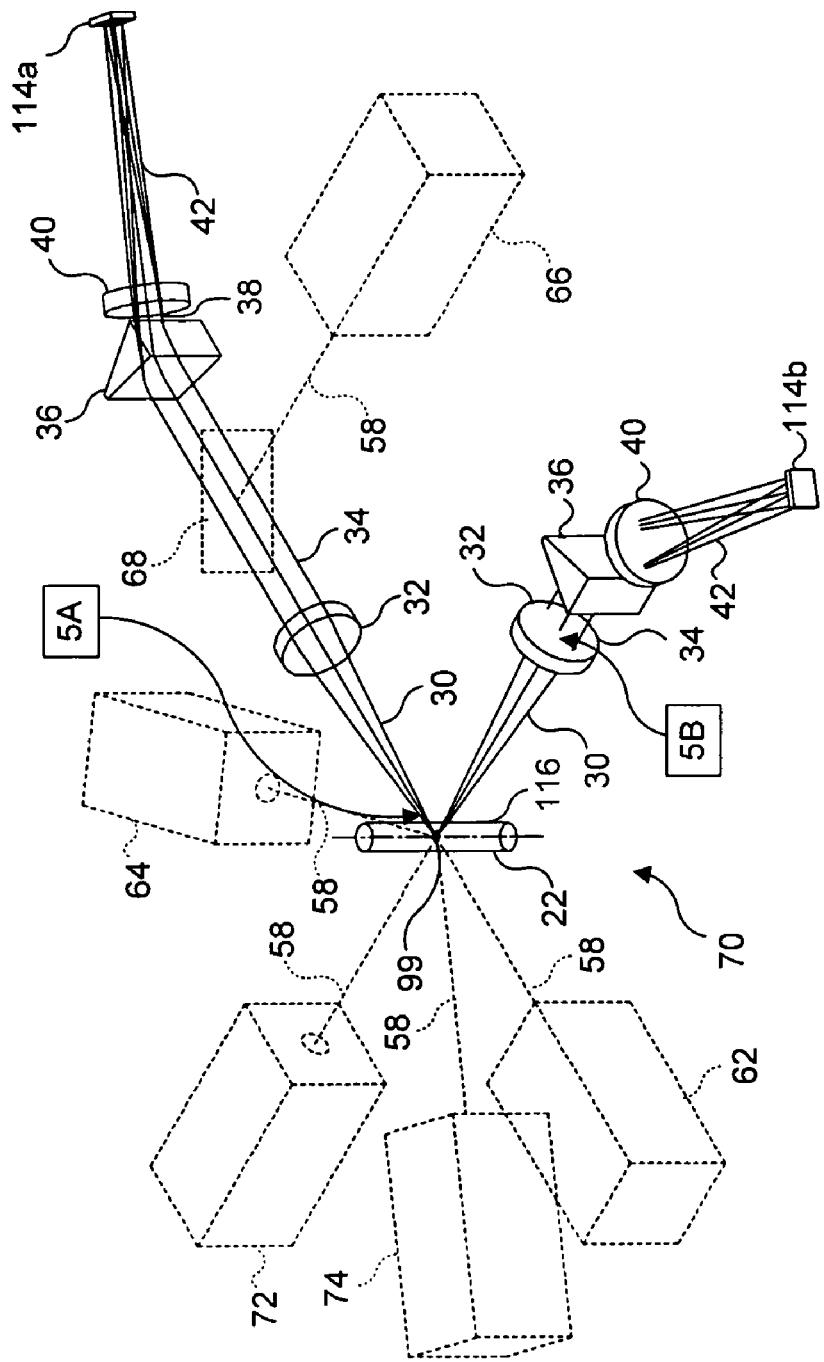
FIG. 2 is a schematic illustration of an exemplary stereoscopic flow imaging system used in accord with the concepts disclosed herein.

Another exemplary flow imaging system embodiment is a stereoscopic arrangement, as illustrated in a flow imaging system 70 of FIG. 2, wherein fluid flow 22 entrains object 99 (such as a cell, but alternatively, a small particle) and carries the object through flow imaging system 70. Light 30 from object 99 passes through collection lens 32 that collects the light, producing collected light 34, which is approximately focused at infinity, i.e., the rays of collected light from collection lens 32 originating at the same location in the object are generally parallel. Collected light 34 enters a prism 36, which disperses the light, producing dispersed light 38. The dispersed light then enters imaging lens 40, which focuses light 42 onto TDI detectors 114*a* and 114*b*. As noted above, either optical distortion element 5A or 5B or adjustable objective lens 102 (or a cuvette/flow cell configured to introduce optical distortion) is included along the optical path between each the object being imaged and the detector. It will typically be desirable to use the same type of optical distortion technique in each optical leg; however, it should be recognized that different distortion techniques can be implemented in each leg, so long as each signal from each detector is processed appropriately to correct for the intentional distortion in each optical leg.

The use of two different optical legs enables the object to be imaged from two different directions, in order to distinguish features that would otherwise overlap when viewed from a single direction. While this embodiment can also be employed for objects on moving substrates, such as microscope slides, it is particularly useful for analyzing multicomponent objects in solution flowing through the system, such as cells containing FISH probes. Such probes appear as point sources of light anywhere within the cell's 3-D nucleus. In some cases, two or more FISH probes may appear in an overlapping relationship along the optical axis of the imaging system. In such cases, one of the FISH probes may obscure the others, making it difficult to determine the number of probes present in the cell. This factor is important in the determination of genetic abnormalities such as trisomy 21, otherwise known as Down syndrome. Single-perspective systems may address this problem by "panning through" the object along the optical axis to acquire multiple image planes in the object. While this method may be effective, it requires a significant amount of time to collect multiple images and cannot be readily applied to a cell in flow. The stereoscopic imaging system 70 in FIG. 2 includes two TDI detectors 114*a* and 114*b*, and their associated optical components, as discussed above, in connection with flow imaging system 150.

By positioning the optical axes of collection lenses 32 for the two TDI detectors so that they are disposed at an angle to each other, for example, about 90 degrees, it is possible to separately resolve the FISH spots imaged from two or more FISH probes on at least one of TDI detectors 114*a* or 114*b*. If two or more FISH probes overlap in regard to the image produced on one of the detectors, they will be separately resolved in the spectrally dispersed images produced on the other TDI detector. Further, the use of two TDI detectors in flow imaging system 70 in what might be referred to as a "stereo or three-dimensional configuration" provides flexibility in the configuration of each leg of the system, including parameters such as the relative TDI readout rates, axial orientations, inclinations, focal plane positions, and magnification. Multiple cells or other objects may be imaged onto each detector simultaneously in the vertical direction. Since the objects move in synchronicity with the signal on the TDI, no gate or shutter is required to prevent blurring of the image. A pulsed or CW light source (without the need for a trigger mechanism to time a pulse coincident with particle arrival in the field of view) is employed. If a pulsed light source is used, the extended field of view in the axis of motion associated with TDI detection enables the cell or object in motion to be illuminated by multiple light pulses during its traversal through the imaging system. In contrast to a frame-based imaging apparatus, a TDI system can produce a single unblurred image of the object that integrates the signal from multiple light pulses. When a CW light source is used, the signal generated by the object will be collected throughout the entire traversal of the object through the field of view, rather than only a small segment in time when a shutter is open. Therefore, the amount of signal collected and imaged on the detector in this exemplary embodiment is substantially greater than that of the prior art frame-based imaging systems. Consequently, the present approach can operate at very high throughput rates with excellent signal-to-noise ratio.

Application of the optical system shown in FIG. 1A in an orthogonal configuration as shown in FIG. 2 provides the ability to determine the location of a source of light within the cell in three dimensions. A single axis EDF system projects light from the cell onto a two dimensional plane without the blur associated with defocus. Therefore, in X-Y-Z Cartesian space, one can readily determine, for example, the location of light coming from the cell in the X and Z axes, assuming the optic axis is parallel to the Y axis. In the Y axis no positional information is available. However, if a second EDF optical system is positioned orthogonal to the Y axis and parallel to the X axis, one can further determine the location of light coming from the cell in the Y axis. A point of light coming from a cell will be imaged onto two detectors simultaneously. Since both detectors collect light from the same Z axis, the Z location of the light on the detectors provides a reference with which to correlate the position of light in all three axes. To unambiguously determine the X, Y and Z location of a point of light, one need only locate the light in the Z axis in the appropriate channel on both detectors, 114*a* and 114*b*, and then assess the position of the light in the X and Y axes on the corresponding detector. For an application involving multiple discrete sources of light within the cell, such a FISH spot enumeration, the techniques disclosed herein may be used to unambiguously count spots from the cell. For molecular co-localization analyses, the same methodology can be applied. However, in this case each molecular species is tagged with a different color marker. Therefore, the same process is applied in two channels of the detector. Since each channel is spatially registered with the other, one can compare the location of light in each channel to assess co-localization of two different molecular species.

Beyond unambiguously locating the position of discrete sources of light from the cell, the concepts disclosed herein can also be used to reconstruct 3-D models of solid bodies and surfaces within the cell. This can be accomplished by dividing the volume of the cell into a set of voxels with a dimension is each axis equal to the pixel size in each axis on the detectors. The intensity of each voxel in the volume can be determined in stepwise fashion. On a given detector, a single pixel, in the X-Z plane for example, represents the sum of voxel intensities for all voxels at that X-Z location along the Y axis. Therefore, to determine the signal in each voxel along the Y axis (at that X-Z location), the total signal from the X-Z pixel would be apportioned into each voxel along the Y axis in accordance with relative proportion of signal present in each pixel along the corresponding row on the Y-Z detector. For example, the signal for an arbitrary set of voxels, X3Z5Y1, $X_3Z_5Y_2$, $X_3Z_5Y_3$, $X_3Z_5Y$ . . . , X3Z5Y100, could be determined as follows. The signal for pixel $X_3Z_5$ in the third column and fifth row on detector X-Z would contain the sum of the signal for all voxels listed above. If this sum were 1000 counts and all 100 pixels on the fifth row of the Y-Z detector contained the same value, than the 1000 count signal would be distributed evenly among all voxels listed. If for example, only the $10^{th}$ and $11^{th}$ pixels contained signal, then all voxel signal levels would be set to zero except for voxels $X_3Z_5Y_{10}$ and $X_3Z_5Y_{11}$. The 1000 count signal would then be distributed into those voxels accordance with the relative signal levels in pixels 10 and 11 on the fifth row of detector Y-Z. In this manner all voxels throughout the volume of a cell could be assigned signal levels to construct a 3-D model of the cell. This model could then be viewed from any angle, and sliced along arbitrary planes, to better visualize the spatial arrangement of cellular components and molecules contained within a cell.

Also illustrated in FIG. 2 are several exemplary positions for light sources, which are useful for different purposes in connection with flow imaging system 70. Light sources are disposed so that light 58 emitted from the source travels toward the object in a direction that is generally aligned with the optical axis of collection lens 32, and the image formed on the TDI detectors thus will not include light absorbed by object 99. Light absorption characteristics of the object can be determined by illuminating the object using these light sources. More specifically, in connection with TDI detector 114a, light source 62 provides illumination of object 99 from a direction so that absorption characteristics of the object can be determined from the image produced on the TDI detector. At the same time, light provided by light source 62 that is scattered from object 99 can be used to produce a scatter image, and spectrally dispersed images on TDI detector 114b. Light source 74 can be employed to produce spectrally dispersed and scattered images on both TDI detectors 114a and 114b. If light sources 62 and 72 are of different wavelengths and an appropriate filter is provided to block the wavelength from the light source aligned with the optical axis of respective collections lenses 32, these two light sources can be used for producing scattered light from the object. For example, suppose light source 72 produces light of a wavelength A that scatters from object 99 and is directed toward TDI detector 114a. By including a filter (not shown) that blocks a wavelength B produced by light source 62, the light at wavelength B will not directly affect the images produced on TDI detector 114a. Similarly, the light from light source 72 would be blocked with an appropriate filter (not shown) so that it does not interfere with the imaging of light produced by light source 62 that is scattered from object 99 onto TDI detector 114b.

Epi light source 66 is also illustrated for use in producing images on TDI detector 114a in connection with partial reflector 68. Light source 64 can be used to generate reflected light to produce images on TDI detector 114a, while scattered light from this source is directed toward TDI detector 114b. These and other possible locations of light sources will be apparent to those of ordinary skill in the art, as appropriate for providing the incident light on the object needed to achieve imaging, depending upon the particular application and information about the object that is desired. Moreover, if the WFC EDF method that is described below in detail is applied to both legs of flow imaging system 70, an accurate 3-D map of the cell can be reconstructed.

While the system of FIG. 2 can be employed to acquire non-EDF images (i.e., it can be used without optical distortion elements 5A or 5B, or adjustable objective 102 or cuvette or cover slip configured to introduce optical distortion), the use of such elements and the post-image processing to partially correct for such distortion enables stereoscopic high definition EDF imaging to be acquired from objects in flow, thereby enabling a large amount of image data to be acquired for a large number of objects much more rapidly than is possible using confocal microscopy.

Extended Depth of Field Imaging

EDF as used herein refers to the capability of imaging more parts of an object in focus than could be imaged using an unmodified imaging system (i.e., an imaging system not modified to achieve the EDF imaging). Such EDF imaging can enable all cellular components within a ten micron or greater depth of field to be imaged in focus. EDF cellular imaging offers an alternative method to developing a confocal-like image projection with the entire cell in focus simultaneously. One of the issues raised by single-plane image capture of microscopic objects is the effect of focus variations on the quality of captured imagery. In particular, if the object to be imaged has fine structures, which are intrinsically in different focal planes, it is not possible to resolve all of the corresponding fine detail in a single planar image. The finer the details to be imaged, the more important this problem becomes, because the size of the smallest features that can be resolved varies inversely with the NA of the optical system, while the depth of focus shrinks faster, as the inverse square of the NA. Thus, EDF imaging can be accomplished at very high speed and eliminates the photo bleaching effects associated with repeated acquisitions of the cell imagery at different planes of focus. EDF imaging can be accomplished in several ways. However, the underlying principal involves the formation of a PSF that is invariant over an expected range of focal positions. For most cell imaging applications, this range is approximately 15 microns. The process of achieving a PSF invariant to focal position increases the size and changes the character of the PSF when compared to the classical best focus point spread. The increased size reduces the ability of the optical system to generate contrast and resolve image detail. However, through de-convolution, the contrast can be largely restored with the benefit of providing "best-focus-like" resolution over a greatly enhanced focal range. The end result is a high-resolution image of the cell with all features simultaneously in focus.

The concepts disclosed herein encompass at least three methods to achieve focus invariant PSFs: (1) a WFC EDF method using a phase plate, for example, a WAVE FRONT CODED™ element provided by CDM Optics, Inc. of Boulder, Colo.; (2) a Spherical Aberration EDF method; and, (3) a Tilted Object Plane Time Delay Integration (TOPTDI) EDF method. Basic principles relating to the TOPTDI EDF method are described in U.S. Pat. No. 6,583,865. The present discussion briefly covers improvements to the TOPTDI method. It should be noted that the WFC EDF technique and the Spherical Aberration EDF technique can be distinguished from the TOPTDI EDF technique, in that the TOPTDI EDF technique acquires data from different focal planes at different times, and thus requires a TDI detector. The WFC EDF technique and the Spherical Aberration EDF technique acquire EDF data simultaneously, and a TDI detector is not required. Use of a TDI detector in implementing the WFC EDF technique and the Spherical Aberration EDF technique is desirable, because the TDI detector increases the amount of light (and therefore data) that can be collected from any object, thereby improving the signal-to-noise ratio of the image; however, each different image acquired by the TDI detector includes an EDF before the integrated image is provided by the detector, in contrast to the TOPTDI implementation.

In summary, all three methods result in a PSF that integrates light from different focal positions in object space, making it relatively insensitive to defocus. This property, in turn, enables de-convolution of the PSF to remove the spatial broadening and contrast loss inherent in the unprocessed image, thereby increasing image fidelity and creating an "in-focus" projected image of the entire cell. However, only the WFC EDF method allows for directed tuning of the optical wave front to optimize the PSF for EDF imaging.

FIG. 4 is a block diagram illustrating the method of providing multi-mode extended depth of field imagery for an object. At a step 160, the method begins with deformation of the optical wave front of light from an object as shown in a step 162. As discussed below in detail, the optical wave front may be deformed by one of a phase plate configured to induce a phase change to light passing through the phase plate, an optical element configured to induce a phase change or distortion to light passing through the optical element, an adjustable objective lens, or a cuvette having different thicknesses at different locations through which the object can be imaged (in at least one embodiment, the cuvette/flow cell includes a face configured to induce distortion, and a face that does not induce distortion, such that rotating the cuvette relative to the imaging optics enables the distortion to be selectively induced). This deformation is performed in such a way that a PSF does not vary substantially across an extended depth of field. Some cellular objects have fine structures that are in different focal planes, and the application of the deformation of the wave front enables all image features within the extended depth of field across the different focal planes to be clearly in focus (at least after image processing has reversed the distortion effects), because the deformation defocuses and expands the depth of field, thereby enabling light from the different focal planes to be simultaneously collected. The method continues in a step 163, wherein the deformed or modified light is dispersed into a plurality of different light beams. Such spectral dispersion enables a dispersed image (or a plurality of spectrally distinct images) of the object to be acquired, generally as indicated in FIG. 1A. An imaging lens is used to generate a dispersed image (or a plurality of images) of the object in a step 164, and the dispersed image is detected in a step 166. The detector of FIG. 1A can thus generate either a plurality of different spectral images (one image per channel), or a single dispersed image (comprising a plurality of spectrally dispersed images).

Optional step 168 indicates that the next step is to determine the PSF of the imaging system that produced the deformed optical wave front. While this step is required to process the raw image data to generate the best quality EDF image, it should be recognized that such a step may not be implemented by a user in some imaging systems, since it could be implemented by a manufacturer of the imaging system, and stored as a known parameter (thus the arrow from step 168 to start). The PSF of the imaging system including the optical distortion element need only be determined once, as long as the configuration of the imaging system remains unchanged. Once a change is made to the optical configuration of the imaging system that changes the imaging system's inherent PSF, the PSF for the modified system would need to again be determined. In a step 170, the image data can be de-convoluted using the PSF to reduce negative effects of the wave front distortion. Then, the extended depth of field image for the object can be produced in a step 172, and the method is complete as shown in a step 174.

Simulation of the WFC EDF Method

The WFC EDF method involves imparting a deformation in the optical wave front of the object via the addition of an optical or distortion element such as a phase plate (or preferably the WAVE FRONT CODED™ element provided by CDM Optics, Inc. of Boulder, Colo.) in the aperture plane of the optical system. The deformation causes light from different focal planes corresponding to a single lateral position in object space to be imaged on the detector plane simultaneously. A significant advantage of the WFC EDF method over the TOPTDI EDF method is the ease with which the system can be converted from standard imaging to EDF imaging. The conversion requires the insertion of the WFC element in the aperture space of the system. The exemplary flow imaging system was designed to place an external image of the aperture in an easily accessible location. For example, a six-position software controlled aperture wheel 157 is shown in FIG. 5, which can be readily disposed in the exemplary imaging system between the objective and the detector. In an exemplary embodiment, the position of the filter wheel can be controlled remotely, so that the internal components of the imaging system do not need to be accessed to selectively switch the imaging system between a standard imaging mode and an EDF imaging mode. Of course, the image processing required in standard mode and EDF mode will be different.

In order to simulate the WFC EDF method, a phase plate was modeled and consists of an optically clear element having a two-axis cubic waveform, where the axes cross orthogonally. A phase plate is an optical component of transparent material placed in the aperture space of an optical system. The phase plate is optically clear and has slight variations in its thickness in order to retard or advance the phase of the wave front relative to the un-deviated wave front. CDM Optics, Inc. has developed the ability to construct phase plates with arbitrary surface shapes and micron-level fabrication tolerances. These phase plates can be used to induce deformations in the optical wave front to potentially provide a more consistent PSF through an extended focal range. Thus, the slight variations in thickness across the plate's surface serve to retard or advance the phase of the wave front. From a geometric perspective, the angular changes in the surface of the element cause ray paths to deviate from their original course to image light from different points along the optic axis for a given lateral position in the image plane. For this simulation, an element was modeled with a sag of the form shown in Equation 1, where n=3.

$$\text{Sag} = \sum_{n=[3,7,9]} a_n \left( \left(\frac{x}{r_0}\right)^n + \left(\frac{y}{r_0}\right)^n \right) \quad (1)$$

A coefficient $a_n$=0.000122 was selected to generate approximately five waves of peak to valley wave front error over the aperture. The element shown as a 3-D rendering in FIG. 6 contains about 6.6 microns of total sag. The element was modeled at an exposed aperture stop in the exemplary flow imaging system to generate the PSFs used in the subsequent analysis as described below. The results are summarized in FIGS. 10A and 10B, described in detail below.

Simulation of the Spherical Aberration EDF Method

The spherical aberration EDF method involves imparting spherical aberration in the wave front by inserting a distortion element between the object and the objective lens in order to induce spherical aberration into the collected imagery. Useful distortion elements include a cover slip (or parallel plate), a custom objective with a correction collar, a custom cuvette having different optical properties in different parts of the cuvette, and switchable optical elements in the image collection path. Spherical aberration causes different regions in the aperture to focus at different points along the optical axis so that points from multiple focal planes in object space are imaged onto one detector plane.

Prior to providing a more detailed discussion of the more complete simulations of the optical system performed with the parallel plate in place, it may first be helpful to present an approximate calculation of the effect of the introduction of a parallel plate of glass on the variation of the focal positions of light entering a microscope objective. Assume that there is a passage of a ray of light R from an object 0 through a parallel plate of glass of thickness t. The ray R leaves the object 0 at an angle Θ to the optical axis. As shown in Equation 2, it is bent according to Snell's Law to an angle φ:

$$\phi = \sin^{-1}\left(\frac{\sin\Theta}{n}\right) \quad (2)$$

where n is the refractive index (approximately 1.5) inside the glass.

Upon leaving the glass, it is bent back to its original angle. While inside the glass, as shown by Equation 3, it has traveled a distance y further from the optical axis than it was at its entry point:

$$y = t\tan\phi = t\tan\left[\sin^{-1}\left(\frac{\sin\Theta}{n}\right)\right]. \quad (3)$$

Tracing the exiting ray R back to where it appears to originate on the optical axis, Equation 4 shows that the focal displacement z' due to the presence of the glass plate is:

$$z' = t - \frac{y}{\tan\Theta}. \quad (4)$$

One useful limit to consider is the case when Θ is very small. In this case it can be shown that:

$$\lim_{\Theta \to 0} z' = t(1 - 1/n). \quad (5)$$

The spherical aberration of the optical system is caused by the fact that z' does not remain constant as Θ ranges from zero up to the NA of the microscope objective, which represents the largest angle ray the objective will accept. The objective used in the exemplary flow imaging system has an NA of 0.75.

FIG. 7 shows the fractional focal offset z'/t as a function of Θ, assuming a nominal glass refractive index n of 1.5. Along the optical axis, z'/t is about 0.33, while at the maximal angle for an NA of 0.75 (the NA of the exemplary flow imaging system), z'/t is about 0.49. The difference between these two fractional focal displacements is approximately 0.16. To set this fractional difference equal to a 10 micron focal depth would require a glass thickness of 1010.16=63 microns. In this experiment, such a thin slip of glass was not readily available, and instead, a commercially available 110 micron thick cover slip was used. The focal offsets introduced by this cover slip varied over a range of 17 microns, which is larger than ideal for covering the depth of a cell nucleus, but still well in the useful range for experimentation.

Now, returning to the simulation, a desirable feature of the Spherical Aberration EDF method capability is selectability, where the spherical aberration can be introduced or not, depending upon the requirements of the particular assay that is being run. The EDF algorithm can then be applied only to imagery collected with the EDF hardware in place. A selectable EDF can be achieved in a number of ways in hardware. First, an insertable cover slip can be disposed between the objective and the cuvette. In an empirical study, the cover glass was held in place on the face of the cuvette by a drop of alcohol to form a temporary rigid optical contact. The introduction of the cover glass creates a known aberration in the optical system, known as spherical aberration. In brief, spherical aberration causes light rays departing a single source at different angles relative to the optic axis to focus at different positions along the optic axis. The immediate result is that imagery becomes more fuzzy. A more subtle effect is that the imagery is less dependent on the exact focal position of the lens relative to the source. If the imagery is enhanced digitally to reduce the fuzziness via de-convolution, while preserving the independence from focal position, an instrument with enhanced depth of field is achieved, at the cost of losing some of the signal-to-noise ratio characteristic of in-focus data from the original instrument. Issues include precision motion requirements and the need to establish and maintain precise angular alignment of the cover slip surfaces orthogonal to the optical axis in the very limited working distance (0.5 mm) between the cuvette and objective available in the exemplary imaging system.

In another Spherical Aberration EDF embodiment, a custom objective with a motorized spherical aberration correction collar can be utilized. Potential problems with such an embodiment include the need to provide a custom optical design, and development of the objective lens and the mechanical interface to drive the correction collar.

In a further Spherical Aberration EDF embodiment, a custom cuvette with different optical thicknesses may be presented to the image collection optical path. Issues with such an embodiment include tight fabrication tolerances on the cuvette wall thicknesses and face perpendicularity, precision motion control within the optical alignment requirements, as well as maintenance of the interface to the fluidic system in the flow cell/cuvette assembly.

In yet another exemplary Spherical Aberration EDF embodiment, switchable optical elements in the image collection optical path may include the final focus lens to the camera/detector, which can be designed with residual spherical aberration and disposed in place of the standard focusing lens during EDF imaging. Issues include the optical design and fabrication of the spherically aberrated lens to maintain parfocality with the standard lens and the motion control system for swapping the lenses in the optical path.

Varying degrees of spherical aberration were modeled to determine the best trade off between contrast loss and depth of field expansion. Evaluation of the PSFs at various focal positions provides a qualitative understanding of the limitations of the Spherical Aberration method. Ideally, the PSF would remain fairly consistent over the focal range of interest. To simulate the Spherical Aberration EDF method, the exemplary flow imaging system was modeled with a decreased flow cuvette thickness to add 1.8 waves of peak-to-peak spherical aberration after refocusing. This optical configuration was then used to model the PSF at the various focus locations required for subsequent analysis. The results are summarized in FIGS. 10A and 10B, described in detail below.

Simulation of the TOPTDI EDF Method

The TOPTDI EDF method can be employed in concert with the TDI detection methods used in the exemplary flow imaging system described in U.S. Pat. No. 6,583,765, the drawings and specification of which are hereby specifically incorporated herein by reference. In this method, the object plane (or detector plane) is tilted such that during the image integration process, the cell scans through a continuous range of focus positions. In other words, the focal plane is tilted relative to the axial flow of the cells such that light from multiple focal planes in object space is integrated during image collection. Either the detector can be tilted relative to a non-tilted flow path for objects being imaged, or a cuvette with a tilted flow path and means for optically correcting for the coma and astigmatism that will be introduced by the tilted reflective surface of the cuvette wall and air interface can be used. In addition, a custom-designed cuvette that has a tilted channel can be employed, thereby eliminating the concern with respect to the astigmatism and coma by ensuring that the cuvette is orthogonal to the collected light. Only the water/glass cuvette is non-orthogonal, providing a decrease in optical aberrations. Introduction of an optical component such as an optical wedge, which effectively tilts the image plane with respect to the camera, may also be utilized. Alternatively, a convolution filter can be used in the beam path, and the known de-convolution algorithm may be utilized to correct for the astigmatism and coma effects.

The technique of modeling a tilted detector methodology to implement a real time "pan through" of focal planes for each object during the TDI integration distance showed potential; however, empirical studies indicated it requires more than a 45 degree tilt of the detector for less than 7 microns of pan through. In addition to implementation difficulties, this degree of tilt induced an anamorphic pixel aspect ratio and decreased collection efficiency. Further empirical studies were performed to investigate tilting the object plane less than the three degrees, in order to pan through 10 microns of focal positions. Unfortunately, initial modeling studies indicated that three degrees of tilt at the air glass interface of the cuvette imparted an unacceptable amount of coma and astigmatism to the wave front.

As an alternative, an improved implementation of the tilted-plane methodology has been developed to achieve the desired EDF performance, without the introduction of excessive off axis aberrations. This method utilizes optical fabrication techniques developed for precision prism manufacturing, to polish the desired tilt angle into the cuvette front surface, relative to the cuvette flow channel, which enables the air/glass interface to remain orthogonal to the objective optical axis, while the three degree tilted surface is placed at the glass/water interface, thereby substantially reducing the residual coma and astigmatism, since the index or refraction mismatch is reduced. This TOPTDI system was modeled, and PSFs were determined for the matrix of field heights and shifted object positions shown below:

| Object Field Height (um) | Object Shift Best Focus +5 um | Object Shift Best Focus Position | Object Shift Best Focus −5 um |
|---|---|---|---|
| 128 | +10 | +5 | 0 |
| 85.3 | +8.332 | +3.332 | −1.668 |
| 42.7 | +6.668 | +1.668 | −3.332 |
| 0 | +5 | 0 | −5 |
| −42.7 | +3.332 | −1.668 | −6.668 |
| −85.3 | +1.668 | −3.332 | −8.332 |
| −128 | 0 | −5 | −10 |

Using the individual PSF from each row within a given column in the matrix above, a PSF was synthesized for a given TOPTDI integration path. These PSFs were then used to compute the through focus MTF plots for the comparison of methodologies. The results are summarized in FIGS. 10A and 10B, as described in detail below.

Processing of Raw Image Data to Produce the Extended Depth of Field Image

Within limitations, the blur associated with the wave front distortion inherent in EDF imaging can be removed through post-processing of the image using de-convolution. De-convolution is the process of enhancing the contrast of a system over some range of frequencies, usually with the objective of overcoming some degradation that has occurred in producing the image data. The difficulty with this procedure is that noise, which is often present at those frequencies, is amplified along with any real signal that may be present. Because of this difficulty, it is usually not desirable to attempt to achieve a perfect de-convolution, which would reconstruct a signal exactly as it was before the degradation. Instead, the attempt should be made to achieve some reasonable level of reconstruction that does not result in too large an amplification of the noise.

Before discussing the exemplary de-convolution methods utilized in processing an image acquired after deforming the optical wave front of light from an object to achieve an EDF, it may be useful to first discuss the spatial resolution and depth of focus in optical systems. Diffraction causes a point source of light to spread out when imaged by an optical system. The resulting intensity pattern, which is called an Airy disk, appears as a bright central spot surrounded by a series of alternating light and dark rings. The intensity pattern is a projection of the PSF of the optical system onto a flat plane. A PSF that produces an Airy disk having a smaller diameter and most of its energy concentrated within the central spot results in a higher spatial resolution. As objects move from the best plane of focus, the Airy disk diameter increases, and the energy spreads out into secondary and tertiary rings, covering a larger area, resulting in relatively poorer spatial resolution. At best focus, the radius (δ) of the central bright spot of the Airy disk is a function the numerical aperture (NA) of the optical system and the wavelength (λ) of light comprising the image, as defined by the following equation:

$$\delta = \frac{0.62\lambda}{NA}. \tag{6}$$

The classical depth of field Δ of an optical system varies inversely as the square of the numerical aperture as defined by the following equation:

$$\Delta = \pm \frac{0.5\lambda}{NA^2}. \tag{7}$$

For a typical moderately high-resolution objective (0.75 NA) used in the center of the visible spectrum (550 nm), the diffraction limited resolution and the depth of focus as defined by Equations 6 and 7 are 0.45 microns and +/−0.49 microns, respectively. As illustrated in FIG. 8, the process of imaging is the mathematical equivalent of convolution. The spatial and intensity information contained within the object (250 line pairs/mm bar target) as shown in the leftmost portion of FIG. 8 is convolved with the PSF of the optical system, resulting in the image shown in the rightmost portion of FIG.

8. The image appears very similar to the object, but some contrast is lost and the edges of the bars are not as sharp as in the original object. This result is caused by the signal content in the original object being spread out due to the PSF of the optical system. The lower thumbnail images in FIG. 9 demonstrate the effect of defocus on both the PSF and the resulting imagery as the focus changes. At 1µ (micron) of defocus, blurring becomes evident and by 4µ of defocus, the optical system has lost the ability to resolve the individual bars in the target. By 8µ of defocus, the bar target is unrecognizable and suffers significantly diminished intensity. Accordingly, when imaged by a 0.75 NA optical system, a cellular feature such as a FISH spot having an area of less than one micron and located six microns away from the plane of best focus will blur into an area covering more than 100 microns, rendering it unrecognizable to a human observer and making automated detection and enumeration difficult at best. This result can occur when viewing FISH probes located at the periphery of the nucleus.

Confocal image stacking techniques avoid this problem by synthesizing an image of the cell with all features simultaneously in focus via the collection of multiple images of the cell at different focal planes. At each focal position, an image is collected by scanning a spot of illumination over the object with a conjugate pinhole located at an intermediate image plane in the collection system. The conjugate pinhole substantially eliminates light from objects outside the focal plane, providing a crisp image of the object structures in the immediate focal plane. By applying image reconstruction algorithms to the stack of imagery, a high-resolution composite image can be generated with the entire cell in focus on a single plane.

As discussed above, the convolution process inherent in imaging can be "undone" through post-processing of the image using de-convolution. This effect can be visually illustrated by reversing the process shown in FIG. 8, where the PSF can be "removed" via de-convolution from the image in the rightmost portion of FIG. 8, such that the image appears more like that of the actual object (the leftmost portion of FIG. 8). With good foreknowledge of the PSF, de-convolution algorithms can be applied to an image to minimize the effect of optical system performance limitations, resulting in a better representation of the original spatial and intensity content of the object. This process works well where there is a high signal-to-noise ratio in the image, and the object is a two-dimensional planar structure with very little depth along the optic axis, such as a semiconductor photo-mask, a printed page, or the bar target shown in FIG. 8. However, in cell analysis applications, the objects being analyzed are inherently 3-D with respect to the depth of field of the optical system. The resulting image of a cell on a detector is composed of many different degrees of point spread depending upon the location of a particular cell structure or probe, with respect to the plane of best focus. The presence of multiple PSFs within the image substantially impairs the de-convolution process. Notwithstanding, it should be noted that 3-D de-convolution of multiple PSFs has been successfully applied to image stacks from standard fluorescence microscopes; however, the process still requires the collection of multiple images of the same cell taken at various positions along the optical axis.

Evaluation of EDF Methods & De-convolution using Modulation Transfer Functions

A convenient method to theoretically evaluate the expected performance of the various EDF methods described above (WFC EDF, Spherical Aberration EDF, and TOPTDI EDF) is to compare their modulation transfer functions (MTF). The typical MTF plot provides a quantitative assessment of contrast over a range of spatial frequencies. For the comparison of the EDF methods discussed above, a single spatial frequency was chosen, and curves were generated for different focus positions. A through-focus MTF plot shows the behavior of the decreasing contrast function on either side of the best focus position. The exemplary flow imaging system utilizes a pixel size of 18 microns at the detector, corresponding to a maximum sampled spatial frequency of 27.8 line pairs/mm at the detector plane. The through-focus MTF plots were calculated at approximately half the maximum resolvable spatial frequency, or 14 line pairs/mm (500 line pairs/mm in object space), over a focal range of +/−10 microns in object space. The optimal performance for an ideal system would be a flat response (i.e., a constant MTF) with maximum contrast over the widest focal depth. FIGS. 10A and 10B show a family of curves representing contrast versus focus for the various EDF methods (without PSF de-convolution), as well as the non-EDF version of the exemplary imaging system.

As shown in FIG. 10A, the standard non-EDF system (solid line) provides the best contrast at the plane of focus. However, the contrast falls off rapidly as the focal position changes. At 2.5 microns of defocus, the standard system provides no contrast in the image. Numerous null contrast points are observed throughout the plotted focal range. The TOPTDI (continuous long dash) EDF method integrates light from focal planes over a range of −5 to +5 microns from best focus. At best focus, the contrast is about 0.2, which is less than one-third of the standard in-focus contrast, but the TOPTDI EDF contrast remains relatively constant over a much wider range of focal positions. The WFC EDF method provides slightly lower contrast than the TOPTDI EDF method, but with a greater enhancement to the depth of focus. The Spherical Aberration EDF method sacrifices more contrast than either of the other EDF methods modeled here, while providing less improvement to the depth of field. It also exhibits a classical non-symmetrical behavior about the best focus position. The lower plot in FIG. 10B illustrates a "modulation normalized" view of the same data, which more clearly shows the relative depth of field enhancements provided by each method.

FIGS. 11A and 12A show simulated point source imagery generated for the various EDF methods using collection parameters associated with the exemplary flow imaging system, including an 18 micron pixel size (0.5 microns in object space), 0.75 counts of random noise per pixel, and the corresponding PSFs for the various focus positions. FIG. 11B shows the results of ten iterations of a Richardson-Lucy de-convolution algorithm applied to each of the EDF images, using the best focus PSF as the de-convolution kernel. The peak intensity (based on a 10 bit A/D conversion) for each thumbnail image is listed above each image. As demonstrated in the upper thumbnail images in FIG. 11B, the PSF de-convolution process can recover a high degree of image contrast (673 counts for TOPTDI at 5 microns of defocus versus 801 counts at best focus in the non-EDF image). The display of each image is scaled for visualization purposes, so that the brightest pixel in the image appears black, and the lowest intensity in the background appears white, causing the background noise to appear higher in the cases where the PSF imagery has a lower peak intensity, particularly in the case of standard imagery at five microns of defocus. It should be understood in all cases the noise level in all pre-de-convolved imagery is the same.

The simulated imagery illustrates the effectiveness of both the TOPTDI EDF and WFC EDF methods in maintaining a constant PSF over an extended focal range. The results are particularly striking when comparing the de-convolved EDF imagery to the standard imagery at five microns of defocus. In FIG. 12A, the peak intensity in the standard image drops to 19 counts at the defocus position, while both the TOPTDI EDF and WFC EDF methods produce peak intensities in excess of 350 counts (FIG. 12B), resulting in an increase in contrast of more than 30 fold (340 counts vs. 9 counts) for both of these EDF methods (over standard imaging). The imagery in the WFC EDF method exhibits some asymmetrical horizontal and vertical artifacts after processing. However, the artifacts are attenuated by more than an order of magnitude in comparison to the primary image. Optimization of this first-generation WFC element and de-convolution kernel is expected to further reduce these artifacts. The induced spherical aberration method fares better under defocus conditions than the standard optical system, but exhibits much lower contrast with defocus than the other two EDF methods: 151 counts (FIG. 12B) vs. ~350 counts (FIG. 12B).

Empirical Evaluation of the WFC EDF Method using Engineered Bead Samples

Simulation of the various EDF methodologies described above offered insights into the advantages and disadvantages of each of the alternative EDF methods. The WFC EDF method was chosen for implementation in an EDF modified version of the empirical imaging system of FIG. 1A, based on its high level of performance in modeling, its flexibility in implementation, and because it offered the ability to custom tailor the degree of depth of field extension to specific applications by employing a choice of any one of multiple WFC elements, each having a different sag function.

To implement and empirically test the WFC method, a crossed cubic WFC element was procured (available from CDM Optics, Inc., Boulder, Colo.) The element was installed at an external aperture stop in the exemplary flow imaging system, and the PSF of the modified imaging system was measured by running a sample of 200 nanometer diameter fluorescent beads (Invitrogen, FluoSpheres™ carboxylate-modified microspheres, 0.2 μm, yellow-green, 505/515 2% solids, F-8811), which was prepared at a 10,000:1 dilution, and run on the modified flow imaging system. Such beads are sufficiently small relative to the pixel size and diffraction limited spot size of the exemplary imaging systems optics so as to be considered as point sources. FIGS. 13A and 13B show a small sampling of the PSF imagery collected during the run. The form of the PSF corresponds very closely to the modeled imagery shown in FIG. 11B. Approximately 1,000 bead images were collected and processed to generate the composite PSF shown in FIG. 13B. Processing included a linear interpolation of each image to remove shift variance caused by under-sampling, and then spatially aligning each image such that the highest intensity appeared in the same pixel for each image. A mean intensity was then calculated for each pixel to generate the composite PSF used in the subsequent image de-convolution step.

To further evaluate the exemplary flow imaging system with WFC EDF imaging, a simple test was devised using 2.5 micron diameter fluorescent beads (as manufactured by Invitrogen Inc., Linear Flow Green), 0.1% intensity. A file was collected containing imagery from nine focus positions spaced 2.0 microns apart. The exemplary flow imaging system's auto-focus control was first enabled to establish the nominal best focus for the beads. The auto-focus control was then disabled, and the stage was positioned at −8.0 microns from best focus. Approximately 200 objects were imaged in darkfield and fluorescence modes at each of the nine focus positions (−8, −6, −4, −2, 0, 2, 4, 6, and 8 microns from best focus), resulting in a file containing 3,600 images over a pan range of 16 microns. Two test files were collected, one using standard imaging, and one using WFC EDF imaging.

FIGS. 14A and 14B show an image gallery of 8 pairs of consecutively selected beads (16 beads total) from each interval of the focus pan. Darkfield (blue) and fluorescence images (green) are shown for each bead. A gallery of bead images collected using standard imagery are shown in FIG. 14A, and a gallery of bead images collected using WFC EDF imaging are shown in FIG. 14B. As is clearly apparent in FIG. 14B, the WFC EDF imagery maintains a much higher degree of focus over the pan range. Focus blur is present in the standard imagery (FIG. 14A) at +/−2 microns of defocus in both darkfield and fluorescent images (objects 701, 702, 1102, and 1103). At +/−4 microns of defocus, blurring is significant (objects 500, 501, 1306, and 1307), and the bead imagery exhibits a marked decrease in peak intensity, as well as a large change in apparent area. By +/−8 microns of defocus, bead images (objects 100, 101, 1707, and 1708) become difficult to discriminate from the background.

In marked contrast, the WFC EDF imagery of FIG. 14B maintains consistent image characteristics throughout the focus pan with both the bead area and intensity remaining relatively constant throughout the pan. This result is particularly evident in the green fluorescent bead imagery shown in the right hand column of FIG. 14B (in a full color image channel 3 of FIG. 14B corresponds to green spectral images). There are some artifacts present at higher levels of defocus in the form of horizontal and vertical lines emanating from the primary bead image and directed toward the top and right hand side of the page. The artifacts largely resemble those generated in the simulation and exhibit much lower intensity than the primary image. These artifacts are a result of slight changes to the PSF with focus and can be minimized with optimizations of the WFC element and de-convolution kernel. Modeling of the non-orthogonal nature of the artifacts has shown that they are also due in part to residual un-corrected spherical aberration in the optical system. The darkfield imagery appears similar in nature to the fluorescence imagery; however, it exhibits stronger de-convolution artifacts, especially at high levels of defocus. This result may be due in part to the fact that the de-convolution kernel was generated from the fluorescent imagery. Future optimizations will include channel specific kernels, balancing of in focus and out of focus imagery for kernel generation, elimination of residual spherical aberration and optimized WFC waveforms; each of which will reduce artifacts.

FIGS. 15A, 15B, 16A, and 16B provide a quantitative analysis of the entire image set from which the imagery in FIGS. 14A and 14B was selected. In these Figures, the peak pixel intensity and area of each object are plotted against object number for both standard images (FIGS. 15A and 15B), and EDF images (FIGS. 16A and 16B), where each dot in a dot plot represents a single bead. A total of 1,800 objects were imaged, including approximately 200 objects acquired at each of nine focal positions, with each focal position separated by 2 microns. Object #1 and object #1800 are therefore spaced 16 microns apart, with the best focus position corresponding to object numbers in the range of 800-1,000. The best focus position was gated using the regions "In Focus pk" or "Infocus Area," with the accompanying mean values for the gated data shown below the corresponding dot plot. In a similar manner, beads from the +/−8 micron focus positions were also gated.

Referring to the dot plots of FIGS. 15A and 16A (i.e., the upper portion of each respective Figure), the dot plot for the standard image set (the upper portion of FIG. 15A) exhibited nearly a 14-fold decrease in average peak intensity (641 counts vs. 44 counts) between the best focus and the "8 um defocus" positions. In contrast the EDF dot plot (the upper portion of FIG. 16A) showed only approximately a 2-fold decrease in average peak intensity (613 counts vs. 287 counts) over the same focus pan. Allowing for the increased focal range and the larger bead size, these results were consistent with the theoretical models for the behavior of peak intensity.

Referring to the dot plots of FIGS. 15B, and 16B (i.e., the upper portion of each respective Figure), the fluorescent EDF imagery of FIG. 16B exhibited a consistent area of approximately 24 pixels throughout most of the focus range, rising to 32 pixels at the +8 micron defocus position. In contrast, the dot plot of the standard imagery (the upper portion of FIG. 15B) exhibited an increase in area of almost 14 times, from 32 pixels to 437 pixels at −8 microns of defocus. Using the area and peak intensity as figures of merit, the exemplary flow imaging system with WFC EDF imaging demonstrates 7-14 times better feature consistency through a depth of field covering the majority of most prokaryotic and eukaryotic cell diameters.

A statistical analysis of the noise contained in the imagery was performed by evaluating the standard deviation in background signal outside the bead image for each individual object. An analysis of over 2,100 objects for each focus pan indicates the median standard deviation in background signal is 0.97 and 1.30 counts, respectively, for the standard and EDF focus pans (identified by σ in each of FIGS. 15A and 16A). The increase in noise of 0.33 counts will degrade the signal-to-noise ratio and therefore, negatively impact the sensitivity of the instrument. However, in comparison to standard imaging, the degradation will be greatest for objects located at the best plane of focus. For objects located away from the best plane of focus, the increased signal maintained via EDF should more than offset the increase in noise. Sensitivity studies of the standard exemplary flow imaging system demonstrate sensitivity superior to standard flow cytometry and indicate an ability to detect as little as 50 molecules of equivalent soluble fluorescein. Further empirical studies of EDF imaging will include a detailed sensitivity study of the EDF collection mode.

Exemplary Post-processing De-convolution of Imagery

In this empirical study, imagery captured in the WFC EDF mode was post processed using a Richardson-Lucy (R-L) iterative de-convolution algorithm to restore fidelity. Starting with a good measurement of the PSF (as modified by the WFC element), the technique seeks to maximize the likelihood of the de-convolved image by using the Expectation Maximization (EM) algorithm. Specifically, it assumes an undistorted image f which is convolved with a PSF h where n denotes the noise associated with the image. Then, EDF modified image g is given by the following equation:

$$g = h \otimes f + n \quad (8)$$

where $\otimes$ is the convolution operator. The R-L algorithm attempts to reconstruct f using the following relationship:

$$\hat{f}_{k+1} = \hat{f}_k \left( h * \frac{g}{h \otimes \hat{f}_k} \right) \quad (9)$$

and where $\hat{f}_k$ is the estimate off after k iterations, and * is the correlation operator. Stability is maintained and convergence achieved in 5 iterations by constraining $\hat{f}_k$ to be nonnegative and by normalizing at every step to conserve energy between g and $\hat{f}_k$.

Evaluation of Chromosome Enumeration Using Standard and EDF Imaging

FISH probes offer a powerful means for detecting and/or quantifying RNA/DNA in a cell and/or cellular organelle. Current slide-based FISH protocols require fixation (e.g., with a polar organic solvent such as methanol) of intact cells. However, this fixation step is not compatible with in-suspension hybridization due to the occurrence of substantial cell loss and cell clumping. Fluorescence In Situ Hybridization-In Suspension (FISH-IS) protocols for performing chromosomal detection on whole cells maintained in fluid suspension have therefore been developed. These protocols enable the cells to be fixed and hybridized without significant loss of cells or cell clumping. FISH-IS has been successfully performed on many different cell types with a variety of probes that are of interest to the clinical and scientific research communities.

Automated chromosome enumeration via FISH or FISH-IS probing is an application for which EDF imaging may confer significant benefits. Defocus causes significant changes in the presentation of probes often blurring one into another or spreading out the signal to such a degree that it is difficult to automatically segment, or visually separate FISH probes from each other or from non-specific binding in the nucleus.

To compare the efficacy of chromosome enumeration between the standard and extended depth of field configurations, cells of the Jurkat human lymphoma line were grown in a suspension culture, then probed using a FISH-IS protocol. Cells were fixed and permeabilized with successive incubations (5 minutes at 4° C.) in 30%, then 70% Carnoy's solution (3:1 methanol:acetic acid) in phosphate buffered saline (PBS). After centrifugation, cells were washed once in 2×SSC (a commonly used buffer including 3 M NaCl, 0.3 M NaCitrate, pH 7.0), then re-suspended in a hybridization buffer containing a Spectrum Green labeled chromosome 8 enumeration probe, according to the manufacturer's directions (Vysis). To hybridize the probe, cells in PCR tubes were exposed to 80° C. for 5 minutes and 42° C. for 2 hours in a DNA thermocycler. 100 ul of 2×SSC was added to the tubes, and the cells were pelleted by centrifugation. The pellets were then re-suspended in 50 ul of 1% paraformaldehyde (in PBS). The sample was then loaded into the exemplary flow imaging system, and a file of 1,000 cells was collected in the standard collection mode (i.e., without the optical deformation element in place). A second file was collected from the same sample immediately thereafter using the WFC EDF collection mode. Both files were analyzed in the same manner using IDEAS™ software to detect and enumerate chromosome 8 in each cell. Image galleries were generated of cells having one, two, or more copies of chromosome 8. The entire collection time for both files was several minutes (including the time required to switch from standard to EDF modes).

The results were automatically analyzed to enumerate copies of the Y chromosome in each cell. Simple classifiers using brightfield imagery were developed to exclude cellular debris, doublet events, and other artifacts from the analysis. A specialized segmentation routine and connected components analysis were performed on the fluorescence imagery to generate a first pass enumeration of chromosomes on single cells. A refinement of the monosomy and disomy classified cells from the first pass enumeration was performed to eliminate false positive events. After the final classification step, the resulting imagery was manually reviewed to qualitatively judge the efficacy of the final classification. This analysis was not intended to be a rigorous examination of the efficacy of the exemplary flow imaging system with EDF for chromosome enumeration. Rather, this experiment was performed to explore an application for which the exemplary flow imaging system with WFC EDF imaging may have a beneficial result.

FIGS. 17A-23D present a brief overview of the analysis of these two files (standard images and EDF images). FIGS. 17A and 17B shows a sampling of 20 cells (10 in each collection mode, i.e., FIG. 17A includes 10 cells obtained using standard imaging and FIG. 17B includes 10 cells obtained using WFC EDF imaging), highlighting some of the challenges in the classification of disomies within the Jurkat sample. The FISH-IS probe imagery is superimposed over a reduced contrast brightfield image of the cells (black and white have been reversed to reduce the amount of black in the image, to facilitate reproduction in this patent application) to provide a sense of scale and verify that the probes are located within the cell. In FIG. 17A (the cell images obtained using standard imaging), at least one of the FISH-IS probes is positioned out of the plane of focus. Consequently, the area of the out of focus probe increases and sometimes engulfs the second probe in the cell. Like the bead imagery shown in FIGS. 14A and 14B, the intensity falls off significantly with defocus, making it difficult to automatically segment the probe or even see it in the image. Image 916 of FIG. 17A includes a cell in which two probes appear to be in close proximity. Slight defocus may have caused these relatively bright probe images to blur into each other, creating what appears to be a single large probe. Although it cannot be specified with certainty, this cell is thought to have two probes due to the total intensity of the probe signal and the elongated shape of the probe. In marked contrast, the EDF imagery presented in FIG. 17B, shows discrete FISH-IS spots even when they are positioned in close proximity to each other, as in images 298 and 935. Unlike the standard collection mode of FIG. 17A, the EDF imagery of FIG. 17B exhibits little to no blurring of FISH-IS spots. This result is also readily apparent when comparing the larger selection of images shown in FIGS. 22A-23D, wherein each FISH labeled chromosome appears as a bright, tightly focused spot.

Development of FISH Spot Enumeration Classifier and Classification Results

In order to determine the efficacy of EDF imaging on the enumeration of chromosomes, an exemplary, simple five-step classifier was developed using the IDEAS™ analysis software. The first two steps involved segmentation and the selection of appropriate objects within the data file for subsequent analysis (the data file includes each image collected from a sample of cells or objects run through the flow imaging system). Object selection was accomplished by plotting the brightfield aspect ratio vs. brightfield area, as shown in the dot plot in FIG. 18. A gate 156 was drawn that encompassed primarily single cells (image 424 being exemplary of a cell in the gated region) and excluded cell fragments/debris (image 845 being exemplary of a cell fragment or debris), and grouped cells (image 75 being exemplary of a grouping or cluster of cells). The gate defined a population named "Cells" containing 595 individual objects, to which subsequent analysis was applied. A similar segmentation and selection process was performed on the standard collection file (i.e., images of cells collected without using EDF imaging) and resulted in 588 individual objects.

The third step in classification (graphically illustrated in FIGS. 19A-19C), involved refinement of the standard segmentation mask to isolate areas of local maxima in each fluorescence cell image. A fluorescence image 89 of a cell, collected in Channel 3, is shown prior to segmentation in FIG. 19A, after initial segmentation (light blue overlay) to identify all areas containing light above background in FIG. 19B, and after morphology segmentation in FIG. 19C (light blue overlay). Morphology masking is a form of contour masking to identify areas of local maxima contained in the initial segmentation mask.

The fourth step in the exemplary classification employed an IDEAS™ feature called "FISH Spots," which uses the morphology mask to perform a connected components analysis to enumerate discrete FISH spots contained within each fluorescent image. The results of this computation and the final gating of disomic cells, the fifth step in the classification, are shown in FIG. 20 for normal images, and in FIG. 21 for EDF images. The upper leftmost portion of FIGS. 20 and 21 respectively correspond to FISH spot enumeration histograms for normal images and EDF images. The first pass analysis using the standard collection mode yielded enumerations of 506 monosomic, 67 disomic, and 15 polysomic (three or more FISH spots) cells as shown in the histogram of FIG. 20 (the leftmost portion of the Figure). In contrast, the first pass enumeration with EDF imaging yielded 421 monosomic, 136 disomic, and 38 polysomic cells, as shown in the histogram of FIG. 21 (the leftmost portion of the Figure). The EDF collection mode therefore produced a 2 times increase in the number of disomy and polysomy-classified cells, with a 17% decrease in monosomic cells. Manual review of the monosomy and disomy-classified cells in both collection modes revealed a significant number of false classifications where hybridization had failed, leaving only non-specific binding of the FISH-IS probes within the nucleus.

To improve classification accuracy, each population of monosomy and disomy-classified cells was further analyzed by plotting peak intensity vs. area for the fluorescence channel. Non-specific binding generally has low peak intensity and large area, and therefore, plots of peak intensity vs. area improve discrimination of nonspecific binding events. Bi-variant plots of this analysis are shown in the middle portion of FIGS. 20 and 21, for standard images and EDF images, respectively. The discrimination boundaries for the standard collection mode are not clear. This result is most evident in a boundary 201 (upper center portion of FIG. 20) drawn to discriminate true and false positives for disomy refinement. The boundary is complex and arbitrary and therefore unsuitable for fully automated classification. In contrast, a boundary 203 (upper center portion of FIG. 21) drawn for the EDF analysis is clear, with the true and false positive populations showing excellent separation. Minor shifts in feature values due to preparation differences or instrument variations will not significantly affect the results of the classifications, making these features and boundaries suitable for fully automated classification. The refined classifications result in 45 (the table in the rightmost portion of FIG. 20) and 96 (the table in the rightmost portion of FIG. 21) disomy events for the standard and EDF collection modes, respectively and a respective 191 (the table in the center portion of FIG. 20) and 189 (the table in the center portion of FIG. 21) monosomy events.

FIGS. 22A-22D display a random set of images from each set of "Refined" and "False Positive" populations defined in FIG. 20 (i.e., standard images). Images in FIG. 22A correspond to standard images of cells categorized as Monosomy Refined in the center plot of FIG. 20. Images in FIG. 22B correspond to standard images of cells categorized as Monosomy False Positive in the center plot of FIG. 20. Images in FIG. 22C correspond to standard images of cells categorized as Disomy Refined in the center plot of FIG. 20. Images in FIG. 22D correspond to standard images of cells categorized as Disomy False Positive in the center plot of FIG. 20.

FIGS. 23A-23D display a random set of images from each set of "Refined" and "False Positive" populations defined in FIG. 21 (i.e., standard images). Images in FIG. 23A correspond to EDF images of cells categorized as Monosomy Refined in the center plot of FIG. 21. Images in FIG. 23B correspond to EDF images of cells categorized as Monosomy False Positive in the center plot of FIG. 21. Images in FIG. 23C correspond to EDF images of cells categorized as Disomy Refined in the center plot of FIG. 21. Images in FIG. 23D correspond to EDF images of cells categorized as Disomy False Positive in the center plot of FIG. 21.

A review of the imagery in FIGS. 22A-23D sheds light on why the EDF collection mode exhibits a two-fold increase in discrimination of disomic events. First, the EDF collection mode largely eliminated focus variation, producing small, bright, tightly focused spots for each hybridization event, as evident in both "Refined" monosomy and disomy populations (FIGS. 23A and 23C). Second, these tightly focused spots dramatically improved the performance of the morphological segmentation algorithm and final classification steps by forming a clear demarcation between well-hybridized probes and non-specific binding events (the plots in the center and rightmost portions of FIG. 21, respectively). The false positive events shown in the galleries of FIGS. 23B and 23D are a result of non-specific binding and result in large segmentation masks with low peak intensities. The use of peak intensity and FISH Spot area effectively discriminates false positive events. By contrast, it is very difficult to discriminate between non-specific binding and highly defocused probes as shown in FIGS. 23B and 23D. Third, by eliminating focus variation, probes located away from the ideal focal plane still appear as small spots, which is in contrast to the probe imagery found in images 213, 228, 245, 255, 257, 275, etc. shown in FIG. 22A or images 15, 251, 279, 465, and 624 etc. of FIG. 22C. Tight focus substantially reduces the probability of events where a defocused probe image engulfs or contacts a second probe image in the cell. With standard imaging, it is a rarity to find imagery similar to images 55 and 247 of FIG. 23C, where two probes are in close proximity and tightly focused. More likely than not, one of these probes will blur, engulfing the other, leading to a misclassification of a disomic event as a monosomic event.

It is likely that future optimizations of the exemplary flow imaging system with extended depth of field will provide for further improvements in image quality and advanced capabilities. Since the exemplary flow imaging system collects imagery in a flow cuvette with image collection access to all four sides of the cell, unlike slide-based imaging systems, there exists the potential to develop a two-axis orthogonal implementation of the architecture described herein. Coupling a two-axis version of the exemplary flow imaging system architecture (i.e., a flow imaging system such as that shown in FIG. 2) with the EDF techniques discussed above would provide a means to perform full 3-D cell mapping and optical sectioning similar to confocal techniques, but at two to three orders of magnitude greater speed and without photobleaching. Each axis would collect an EDF projection of the cell from orthogonal perspectives, enabling a 3-D reconstruction of the cell, as is done in optical tomographic methods. However, unlike confocal techniques, this method would provide an isometric perspective with consistent resolution in all axes. Since the cells would be mapped in a single pass, photobleaching would be minimized and, with sufficient image processing capacity, tens of thousands of cells could be analyzed in several minutes. FIG. 2 schematically illustrates such a stereoscopic imaging system.

The high-resolution EDF flow imaging techniques disclosed herein should find beneficial application in the following types of image-based analytical studies: (1) FISH-IS, which provides high throughput automated spot counting of FISH-probed cells in suspension; (2) Cell Cycle and Mitosis Analysis for quantization and visualization of DNA-stained cells; (3) Stem Cell Imaging for visualization of rare cells; (4) Phagocytosis for quantitative analysis of macrophage activity; and (5) Cell Signaling for imaging and quantization of T-cell/antigen-presenting cell conjugates. Moreover, one of the most promising applications is the high throughput genetic testing of cells using FISH-IS cell probing technique. Standard FISH is increasingly being used for such purposes as prenatal genetic testing, qualifying patients for breast cancer treatment with Herceptin™, and leukemia lymphoma testing. Current methods of FISH probing are typically performed manually on a small number of cells per test, which makes them unsuitable for identifying and classifying cancer or other target cells that may be present at less than five percent of the sample. The FISH-IS technique, in connection with the exemplary EDF flow imaging system's ability to analyze tens of thousands of cells, will allow the detection of rare target cells for clinical applications like cancer detection as well as the correlation of genetic and phenotypic traits in target validation studies.

Further improvements relate to optimizing the PSF used for image reconstruction. More specifically, a custom model PSF for each channel will be created, to take into account different focal depths and aberrations which may be present at different wavelengths. Thus, different correct PSFs will be used for post image processing (i.e., image de-convolution). Such PSFs will be tailored to work with a given depth of field, by collecting data from beads over the full depth for which the system is expected to perform.

Exemplary Computing Environment

As discussed above, a key aspect of the EDF imaging techniques disclosed herein involves post image acquisition processing to enhance the image data, to achieve an EDF image. Such image processing corrects for errors introduced by the PSF of the imaging system, and the intentional distortion of the optical wave front from the object. Preferably, such image processing is a de-convolution process based on the PSF of the imaging system (or other corrective PSFs, generally as discussed immediately above). FIG. 24 schematically illustrates an exemplary computing system 250 suitable for use in implementing the method of FIG. 4 (i.e., for executing step 170 of this method). Exemplary computing system 250 includes a processing unit 254 that is functionally coupled to an input device 252 and to an output device 262, e.g., a display (which can be used to output a result to a user, although such a result can also be stored). Processing unit 254 comprises, for example, a central processing unit (CPU) 258 that executes machine instructions for carrying out an analysis of data collected in connection with operation of the vehicle to determine upon which one of the plurality of predefined routes the vehicle has been operated in conjunction with acquisition of the data. The machine instructions implement functions generally consistent with those described above with respect to step 170 of FIG. 4, as well as those at other locations herein with respect to image processing to enhance the EDF image. CPUs suitable for this purpose are readily available, for example, from Intel Corporation, AMD Corporation, Motorola Corporation, and other sources, as will be well known to those of ordinary skill in this art.

Also included in processing unit 254 are a random access memory (RAM) 256 and non-volatile memory 260, which can include read only memory (ROM) and may include some form of memory storage, such as a hard drive, an optical disk (and drive), etc. These memory devices are bi-directionally coupled to CPU 258. Such storage devices are well known in the art. Machine instructions and data are temporarily loaded into RAM 256 from non-volatile memory 260. Also stored in the memory are an operating system software and ancillary software. While not separately shown, it will be understood that a generally conventional power supply will be included to provide electrical power at a voltage and current level appropriate to energize the components of computing system 250.

Input device 252 can be any device or mechanism that facilitates user input into the operating environment, including, but not limited to, one or more of a mouse or other pointing device, a keyboard, a microphone, a modem, or other input device. In general, the input device will be used to initially configure computing system 250, to achieve the desired processing (e.g., to process image data to produce images as discussed above). Configuration of computing system 250 to achieve the desired processing includes the steps of loading appropriate processing software into non-volatile memory 260, and launching the processing application (e.g., loading the processing software into RAM 256 for execution by the CPU) so that the processing application is ready for use. Output device 262 generally includes any device that produces output information, but will most typically comprise a monitor or computer display designed for human visual perception of output. Use of a conventional computer keyboard for input device 252 and a computer display for output device 262 should be considered as exemplary, rather than as limiting on the scope of this system. Data link 264 is configured to enable image data collected from a flow imaging system to be introduced into computing system 250 for subsequent image processing as discussed above. Those of ordinary skill in the art will readily recognize that many types of data links can be implemented, including, but not limited to, universal serial bus (USB) ports, parallel ports, serial ports, inputs configured to couple with portable memory storage devices, FireWire (conforming to I.E.E.E. 1394 specification) ports, infrared data ports, wireless data ports such as Bluetooth™, network connections such as Ethernet ports, and Internet connections.

Although the concepts disclosed herein have been described in connection with the exemplary form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for generating a three-dimensional map of an object, wherein the three-dimensional map exhibits a first extended depth of field along a first axis and a second extended depth of field along a second axis, comprising the steps of:
   (a) collecting light from the object along both a first collection path comprising the first axis and a second collection path comprising the second axis, where the first axis and the second axis are not parallel;
   (b) deforming an optical wave front of light from the object to produce modified light, such that light in both the first collection path and the second collection path comprises modified light, and a point spread function (PSF) of an imaging system used to collect the modified light is substantially invariant across the first extended depth of field and the second extended depth of field;
   (c) focusing modified light from the first collection path to produce a first image of the object, the first image being formed by light simultaneously collected from a first plurality of different focal planes along the first axis, the first plurality of different focal planes comprising the first extended depth of field;
   (d) detecting the first image of the object using a first detector to generate first image data;
   (e) focusing modified light from the second collection path to produce a second image of the object, the second image being formed by light simultaneously collected from a second plurality of different focal planes along the second axis, the second plurality of different focal planes comprising the second extended depth of field;
   (f) detecting the second image of the object using a second detector to generate second image data;
   (g) processing the first and second image data to reduce artifacts introduced by deforming the optical wave front, to produce a first corrected extended depth of field image corresponding to the first collection path, and a second corrected extended depth of field image corresponding to the second collection path; and
   (h) using the first corrected extended depth of field image and the second corrected extended depth of field image to produce the three-dimensional model of the object.

2. The method of claim 1, further comprising the step of analyzing the three-dimensional model of the object to determine at least one characteristic of the object.

3. The method of claim 1, wherein there is relative motion between the object and the imaging system used to produce the first image of the object and the second image of the object.

4. The method of claim 3, wherein the object is entrained in a flow of fluid.

5. The method of claim 1, wherein at least one of the first extended depth of field and the second extended depth of field comprises about fifteen microns.

6. The method of claim 1, wherein the step of processing the image data comprises the steps of:
   (a) determining the PSF of the imaging system configured to deform the optical wave front for the first collection path and the second collection path;
   (b) using the PSF function for the first collection path to produce the first corrected extended depth of field image of the object; and
   (c) using the PSF function for the second collection path to produce the second corrected extended depth of field image of the object.

7. The method of claim 1, wherein processing the image data comprises the step of de-convolving the first and second image data.

8. The method of claim 7, wherein the step of de-convolving the image data reduces spatial broadening and contrast loss induced by the step of deforming the optical wave front.

9. The method of claim 1, wherein the step of deforming the optical wave front comprises the step of using an optical element to deform the optical wave front.

10. The method of claim 9, wherein the optical element comprises at least one element selected from the group consisting essentially of:
   (a) a phase plate configured to induce a phase deviation in the optical wave front;
   (b) an optical element configured to induce a spherical aberration in light received from the object; and
   (c) a cuvette having different optical thicknesses at different locations, such that imaging through the different locations of the cuvette induces different degrees of wave front deformation.

11. The method of claim 9, wherein the step of using an optical element to deform the optical wave front comprises the steps of:
(a) using a first optical element to modify light for the first collection path; and
(b) using a second optical element to modify light for the second collection path.

12. The method of claim 1, further comprising the step of spectrally dispersing the light in the first collection path before focusing the modified light to produce the first image, such that the first image comprises a spectrally dispersed image.

13. The method of claim 12, further comprising the step of spectrally dispersing the light in the second collection path before focusing the modified light to produce the second image, such that the second image comprises a spectrally dispersed image.

14. The method of claim 1, wherein the step of deforming the optical wave front comprises the step of modifying the aberration correction of an objective lens.

15. A method for generating a stereoscopic view of an object, while there is relative motion between the object and an imaging system used to produce the stereoscopic view, wherein the stereoscopic view exhibits a first extended depth of field along a first axis and a second extended depth of field along a second axis, where the first axis and the second axis are not parallel, comprising the steps of:
(a) using a first optical element to induce an aberration in an optical wave front of light from the object to produce a first modified light along a first collection path, such that a point spread function (PSF) of the imaging system as modified by the first optical element is substantially invariant across the first extended depth of field;
(b) using a second optical element to induce an aberration in an optical wave front of light from the object to produce a second modified light along a second collection path, such that a PSF of the imaging system as modified by the second optical element is substantially invariant across the second extended depth of field;
(c) focusing the first modified light to produce a first image of the object that includes light simultaneously collected from a plurality of different focal planes along the first axis, and focusing the second modified light to produce a second image of the object that includes light simultaneously collected from a plurality of different focal planes along the second axis;
(d) detecting the first image of the object and the second image of the object to generate image data;
(e) processing the image data to reduce artifacts introduced by deforming the optical wave front with the first and second optical elements, to produce a first corrected extended depth of field image of the object and a second corrected extended depth of field image of the object; and
(f) using the first corrected extended depth of field image of the object and the second corrected extended depth of field image of the object to generate the stereoscopic view of the object.

16. The method of claim 15, wherein the step of detecting the first image of the object and the second image of the object comprises the step of using a time delay integration detector to collect each image over a period of time, while the object moves relative to the imaging system.

17. The method of claim 15, further comprising the step of dispersing the first modified light into a plurality of light beams, such that:

(a) the step of focusing the first modified light comprises the step of focusing each of the light beams to produce a respective first image corresponding to that light beam, each respective first image being formed from the first modified light simultaneously collected from the plurality of different focal planes along the first axis;
(b) the step of detecting the first image comprises the step of detecting each respective first image of the object to generate image data; and
(c) the step of processing the image data comprises the step of processing the image data for each respective first image to reduce artifacts introduced by deforming the optical wave front, to produce the first corrected extended depth of field image of the object for each respective first image.

18. The method of claim 17, further comprising the step of analyzing each respective first image to determine at least one characteristic of the object.

19. The method of claim 17, wherein the step of processing the image data comprises the steps of:
(a) determining the PSF of the imaging system as modified by the first optical element configured to deform the optical wave fronts along the first collection path; and
(b) using the PSF function to de-convolve each respective first image, thereby reducing spatial broadening and contrast loss induced by the PSF of the imaging system as modified by the first optical element.

20. The method of claim 15, wherein at least one of the first optical element and the second optical element comprises at least one element selected from the group consisting essentially of:
(a) a phase plate configured to induce a phase deviation in an optical wave front;
(b) an optical element configured to induce a spherical aberration in light from the object; and
(c) a cuvette having different optical thicknesses at different locations, such that imaging through the different locations of the cuvette induces different degrees of wave front deformation.

21. The method of claim 15, wherein the step of deforming the optical wave front comprises the step of modifying the aberration correction of an objective lens.

22. An imaging system adapted to perform extended depth of field imaging of an object, to acquire a first extended depth of field image of the object using light moving away from the object in a first direction, and a second extended depth of field image of the object using light moving away from the object in a second direction, where the first and second directions are different, such that a three-dimensional model of the object can be generated using the first and second extended depth of field images, the system comprising:
(a) a first optical element configured to deform an optical wave front of light moving away from the object in the first direction, and a second optical element configured to deform an optical wave front of light moving away from the object in the second direction, such that a point spread function (PSF) of the imaging system as modified by the first and second optical elements is substantially invariant across a first extended depth of field associated with light moving away from the object in the first direction and a second extended depth of field associated with light moving away from the object in the second direction;
(b) a first collection lens disposed so that light moving away from the object in the first direction passes through the first collection lens and travels along a first collection path, and a second collection lens disposed so that light moving away from the object in the second direction passes through the second collection lens and travels along a second collection path;

(c) a first imaging lens disposed to receive light travelling along the first collection path that has been deformed by the first optical element, thus producing a first deformed extended depth of field image;

(d) a second imaging lens disposed to receive light travelling along the second collection path that has been deformed by the second optical element, thus producing a second deformed extended depth of field image;

(e) a first detector disposed to receive the first deformed extended depth of field image produced by the first imaging lens, producing an output signal that is indicative of the first deformed extended depth of field image, and a second detector disposed to receive the second deformed extended depth of field image produced by the second imaging lens, producing an output signal that is indicative of the second deformed extended depth of field image; and (f) a processor configured to:
  (i) manipulate the output signal from the first detector to reduce artifacts introduced by the first optical element to deform the optical wave front of light from the object in the first collection path, to produce the first extended depth of field image of the object; and
  (ii) manipulate the output signal from the second detector to reduce artifacts introduced by the second optical element to deform the optical wave front of light from the object in the second collection path, to produce the second extended depth of field image of the object.

23. The system of claim 22, wherein at least one of the first optical element and the second optical element comprises one element selected from the group consisting essentially of:
  (a) a phase plate configured to induce a phase deviation in the optical wave front;
  (b) an optical element configured to induce a spherical aberration in light from the object; and
  (c) a cuvette having different optical thicknesses at different locations, such that imaging through the different locations of the cuvette induces different degrees of wave front deformation.

24. The system of claim 22, wherein at least one of the first optical element and the second optical element configured to deform the optical wave front of light moving away from the object comprises an adjustable objective lens, such that the aberration of the objective lens can be modified to deform the optical wave front of light from the object.

25. The system of claim 22, wherein at least one of the first optical element and the second optical element is selectively positionable, such that in a first position, that optical element deforms the optical wave front, thereby enabling extended depth of field imaging, while in a second position, that optical element does not deform the optical wave front, thereby enabling non-extended depth of field imaging.

26. The system of claim 22, wherein the processor is configured to use the PSF as modified by the first optical element and the second optical element to de-convolve the first and second output signals, thereby reducing spatial broadening and contrast loss induced by the PSF as modified by each optical element.

27. The system of claim 22, wherein the processor is configured to use the first extended depth of field image and the second extended depth of field image to generate the three-dimensional map of the object.

28. The system of claim 22, further comprising a first dispersion element configured to disperse light traveling along the first collection path before the first imaging lens produces the first deformed extended depth of field image, such that the first deformed extended depth of field image comprises one of:
  (a) a single dispersed image; and
  (b) a plurality of individual dispersed images.

29. The system of claim 28, further comprising a second dispersion element configured to disperse light traveling along the second collection path before the second imaging lens produces the second deformed extended depth of field image, such that the second deformed extended depth of field image comprises one of:
  (a) a single dispersed image; and
  (b) a plurality of individual dispersed images.

30. An imaging system adapted to perform extended depth of field imaging of an object in order to produce a stereoscopic image of the object, while there is relative movement between the object and the imaging system, comprising:
  (a) a first optical element configured to deform an optical wave front of light moving away from the object in a first direction, thereby producing first modified light, and a second optical element configured to deform an optical wave front of light moving away from the object in a second direction, such that a point spread function (PSF) of the imaging system as modified by each optical element is substantially invariant across a first extended depth of field associated with light moving away from the object in the first direction and a second extended depth of field associated with light moving away from the object in the second direction;
  (b) a first collection lens disposed so that light moving away from the object in the first direction passes through the first collection lens and travels along a first collection path, and a second collection lens disposed so that light moving away from the object in the second direction passes through the second collection lens and travels along a second collection path;
  (c) a first dispersing component disposed in the first collection path so as to receive the light that has passed through the first collection lens, dispersing the light into a plurality of separate light beams, each light beam being directed away from the first dispersing component in a different predetermined direction, and a second dispersing component disposed in the second collection path so as to receive the light that has passed through the second collection lens, dispersing the light into a plurality of separate light beams, each light beam being directed away from the second dispersing component in a different predetermined direction;
  (d) a first imaging lens disposed to receive the light beams from the first dispersing component, producing a plurality of images, each image corresponding to one of the light beams and being projected by the first imaging lens toward a different predetermined location, and a second imaging lens disposed to receive the light beams from the second dispersing component, producing a plurality of images, each image corresponding to one of the light beams and being projected by the second imaging lens toward a different predetermined location;
  (e) a first detector disposed to receive the plurality of images produced by the first imaging lens, producing a first output signal that is indicative of imaging light moving away from the object in the first direction at a plurality of different focal planes, and a second detector disposed to receive the plurality of images produced by the second imaging lens, producing a second output signal that is indicative of imaging light moving away from the object in the second direction at a plurality of different focal planes; and (f) a processor configured to manipulate the first output signal and the second output signal to reduce artifacts introduced by the first optical element and the second optical element configured to deform the optical wave fronts of light from the object, to produce a plurality of first corrected extended depth of field images of the object for light moving away from the object in the first direction, and a plurality of second corrected extended depth of field images of the object for light moving away from the object in the second direction, and to use the plurality of first corrected extended depth of field images and the plurality of second corrected extended depth of field images to produce the stereoscopic image of the object.

31. The system of claim 30, wherein at least one of the first optical element and the second optical element is a phase plate configured to induce a phase deviation in the optical wave front.

32. The system of claim 31, wherein the phase plate is disposed proximate a numerical objective of the imaging system.

33. The system of claim 30, wherein at least one of the first optical element and the second optical element is configured to induce a spherical aberration in light from the object.

34. The system of claim 30, wherein at least one of the first optical element and the second optical element is a cuvette having different optical thicknesses at different locations, such that imaging through the different locations of the cuvette induces different degrees of wave front deformation.

35. The system of claim 30, wherein at least one of the first optical element and the second optical element is selectively positionable, such that in a first position, that optical element deforms the optical wave front, thereby enabling extended depth of field imaging, while in a second position, that optical element does not deform the optical wave front, thereby enabling non-extended depth of field imaging.

* * * * *